(12) United States Patent
Sisbarro

(10) Patent No.: US 6,217,815 B1
(45) Date of Patent: Apr. 17, 2001

(54) METHOD AND APPARATUS FOR MANUFACTURING PROPHYLACTIC DEVICES

(75) Inventor: Frederick P. Sisbarro, Wayne, NJ (US)

(73) Assignee: Carter-Wallace, Inc., New York, NY (US)

( * ) Notice: Subject to any disclaimer, the term of this patent is extended or adjusted under 35 U.S.C. 154(b) by 0 days.

(21) Appl. No.: 09/095,330

(22) Filed: Jun. 10, 1998

(51) Int. Cl.⁷ .................................................. B29C 41/14
(52) U.S. Cl. .................. 264/440; 264/37.18; 264/39; 264/85; 264/129; 264/130; 264/131; 264/236; 264/237; 264/255; 264/301; 264/303; 264/305; 264/306; 264/310; 264/347; 264/37.1; 264/438
(58) Field of Search ................ 264/39, 37.1, 37.18, 264/85, 255, 301, 303, 305, 306, 310, 236, 237, 234, 345, 347, 348, 129, 130, 131, 438, 440

(56) References Cited

U.S. PATENT DOCUMENTS

| | | |
|---|---|---|
| 2,025,029 | 12/1935 | Ford . |
| 2,128,827 | 8/1938 | Killian . |
| 2,139,545 | 12/1938 | Gammeter . |
| 2,146,293 | 2/1939 | Gammeter . |
| 2,233,555 | 3/1941 | Reisinger . |
| 2,249,755 | 7/1941 | Fingado et al. . |
| 2,288,444 | 6/1942 | Fingado et al. . |
| 2,297,459 | 9/1942 | Dichter . |
| 2,299,269 | 10/1942 | Gammeter . |
| 2,351,202 | 6/1944 | Hahne . |
| 2,353,256 | 7/1944 | Maywald, Jr. . |
| 2,482,418 | 9/1949 | Jenkins . |
| 2,712,161 * | 7/1955 | Moss ................................... 264/303 |
| 2,731,668 | 1/1956 | Miner . |
| 2,814,069 * | 11/1957 | Lenhart ..................................... 74/55 |
| 2,814,834 | 11/1953 | Hess et al. . |
| 2,889,291 | 6/1959 | Moore . |
| 2,923,598 | 2/1960 | Reis, Jr. et al. . |
| 2,973,333 | 2/1961 | Katz et al. . |
| 3,166,791 | 1/1965 | Miller et al. . |
| 3,270,710 | 9/1966 | Johnson et al. . |
| 3,278,991 | 10/1966 | Peternell et al. . |
| 3,694,117 | 9/1972 | Gould et al. . |
| 4,377,603 * | 3/1983 | Itoh et al. ............................... 427/25 |
| 4,495,229 | 1/1985 | Wolf et al. . |
| 4,684,490 | 8/1987 | Taller et al. ......................... 264/296 |
| 4,817,593 | 4/1989 | Taller et al. . |
| 4,855,169 * | 8/1989 | McGlothlin et al. ............... 428/35.2 |
| 4,895,101 | 1/1990 | Knorr . |
| 4,917,850 | 4/1990 | Gray . |
| 4,988,277 * | 1/1991 | Wichterle et al. .................... 425/435 |
| 4,993,935 | 2/1991 | Stevanovich . |
| 5,112,555 * | 5/1992 | Morelli et al. .................... 264/271.1 |
| 5,391,343 * | 2/1995 | Dreibelbis et al. .................. 264/216 |

* cited by examiner

Primary Examiner—Jan H. Silbaugh
Assistant Examiner—Suzanne E McDowell
(74) Attorney, Agent, or Firm—Kenneth Watov; Watov & Kipnes, P.C.

(57) ABSTRACT

Prophylactic devices are made in an inert atmosphere by cooling mandrels on which the devices are to be deposited, dipping the mandrels into a polymeric material in a solvent/carrier and a mold release agent, rotating the mandrels during and after the dipping, and evaporating the solvent after dipping. The apparatus includes an air lock between a section in which these functions are performed and a section located in an air atmosphere for removing the devices from the mandrels, followed by cleaning the mandrels for use in a subsequent production run for making devices.

60 Claims, 31 Drawing Sheets

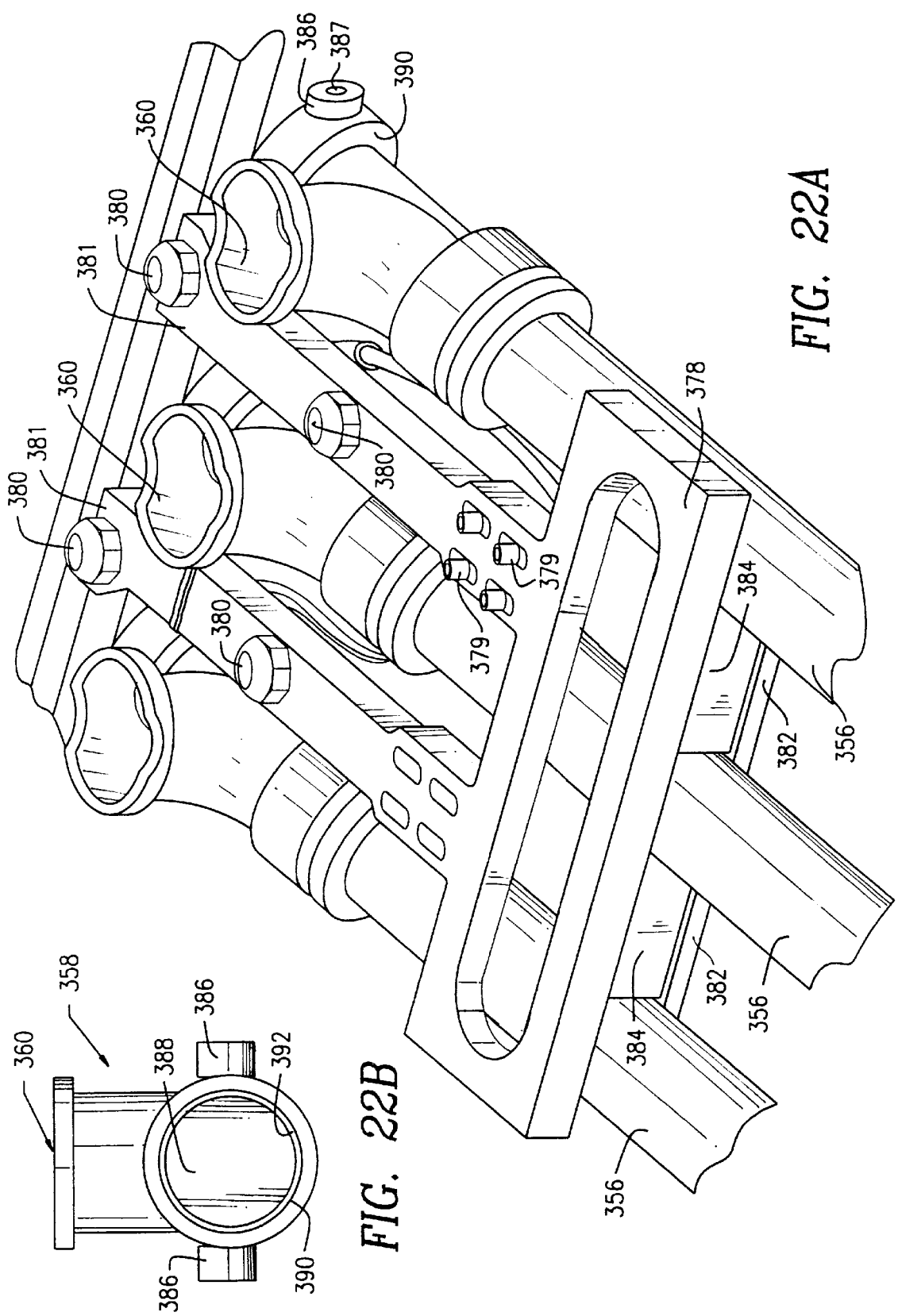

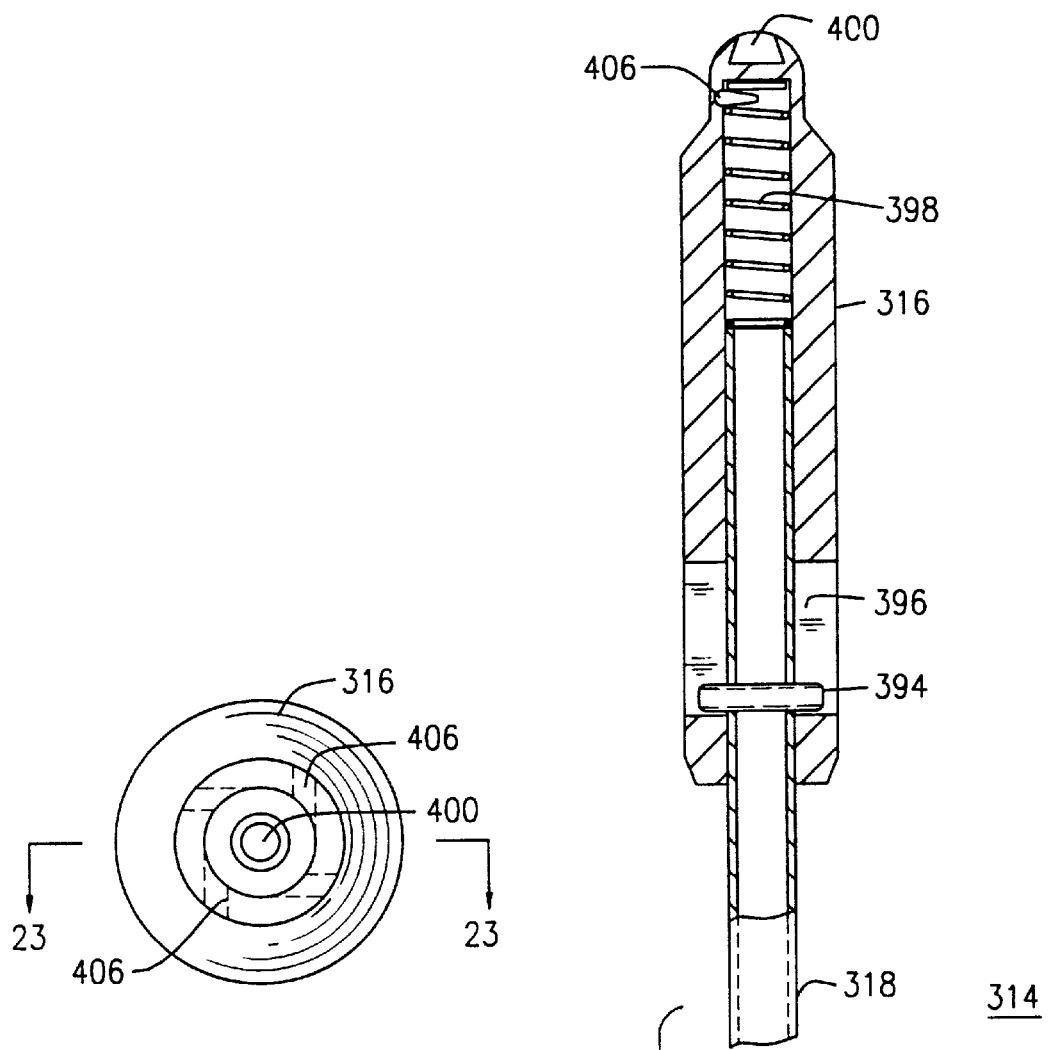
FIG. 24
FIG. 23
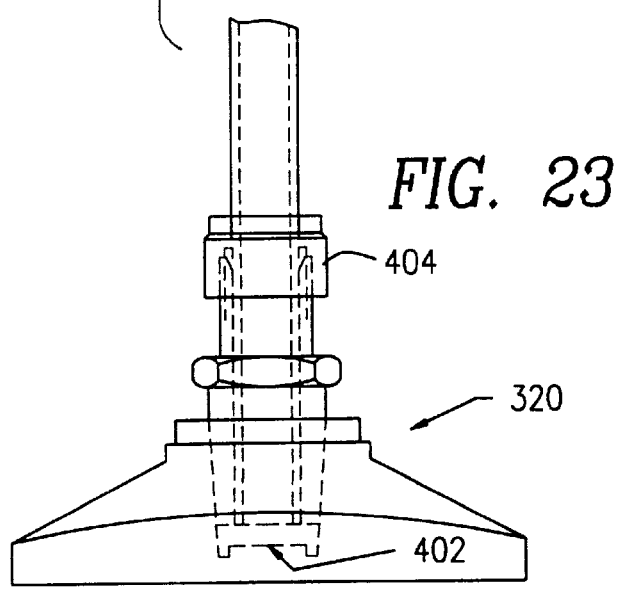

METHOD AND APPARATUS FOR MANUFACTURING PROPHYLACTIC DEVICES

RELATED APPLICATION

This Application is related to Ser. No. 09/095,345, filed on the same day herewith, filed Jun. 10, 1998, now U.S. Pat. No. 6,106,748, entitled "Method And Apparatus For Removing Prophylactic Devices From Mandrels", and assigned to the same Assignee as the present Application

FIELD OF THE INVENTION

The field of the present invention relates to apparatus and methods for making prophylactic devices, and more particularly to making such prophylactic devices from polyurethane.

BACKGROUND OF THE INVENTION

Prophylactic devices are used to prevent the transfer of infection, bacteria and viruses from an environment to a body member on which the device is mounted. Prophylactic devices include but are not limited to catheters, valves, gloves, and so forth. For example, condoms are used to protect the user from venereal diseases and for birth control, and surgical gloves are used to protect the user from infection. In order to allow the protected body member to move freely and to respond to external stimulus, the device must be as thin as possible, but this reduces the protection it provides. For many years prophylactic devices have been made of latex rubber, but when a latex condom is sufficiently thin, it reduces overall strength, is subject to breakage, and there is an increased risk that it will have pin holes that are large enough to permit the passage of viruses such as the HIV. Accordingly, latex condoms must be manufactured and tested with great care and consequent expense. Also, some people are allergic to latex.

It has been found that prophylactic devices made of polyurethane, in contrast to latex, can be very thin so as to provide a good sense of feel while at the same time being very strong, and free from pinholes. Also, polyurethane due to its synthetic nature is typically more nonallergenic than latex.

In U.S. Pat. No. 4,684,490 a method for manufacturing condoms is described in which a mandrel having the general shape and dimensions of a condom is dipped into a solvent solution of a polyurethane polymer and heated in air after being withdrawn therefrom so as to dry the polyurethane. The dried polyurethane which now forms a condom is then removed from the mandrel.

SUMMARY OF THE INVENTION

In accordance with the overall method used in this invention, mandrels having the general shape of the prophylactic device being manufactured are cleaned and subjected to cooling before being dipped into polyurethane or other suitable polymers dissolved in tetrahydrofuran (THF) for example. Other solvents or carriers such as dimethylfluorene (DMF), methyl ethyl ketone (MEK), dimethyl sulfoxide (DMSO), dimethylacetimide (DMAC), alcohols, chlorinated hydrocarbons, ketones, ethers, water ($H_2O$), or any other organic solvents known in the art, and blends of such solvents, can also be used. THF is preferred for use in this invention partly because of its high solubility and easy removal or release from the finished film.

After dipping, the mandrels are rotated so as to produce a uniform film of a desired thickness profile and subjected to an elevated temperature so as to drive off the solvent. In a preferred method, the process is repeated starting with progressive cooling, followed by a second dip so that a second film of polyurethane is formed with the first film on the mandrel. The two films tend to become homogenous. Since THF tends to be highly flammable and potentially explosive in an oxygen atmosphere, the steps just described are carried out in a pressurized explosion resistant atmosphere maintaining oxygen below levels to support combustion.

The invention also includes a system for carrying out the aforesaid method in which pallets having mandrels mounted therein are transported through cleaning stations before being transported through a plurality of progressive cooling chambers to a dipping chamber in which there is a reservoir of polyurethane material dissolved in tetrahydrofuran. The viscosity of the solution is maintained in a desirable range by mixing or agitating it at a controlled temperature and keeping the concentration of THF within a given range. It is important that the rate at which the mandrels are lowered into and raised from the solution be precisely controlled, smooth and that there be no vibration. The pallets of mandrels are then rotated as much as 360° about an axis in the plane of the pallet, first in the dipping chamber, and then in a rotation chamber. Bidirectional rotation may be used in some applications. While in these chambers the mandrels themselves are also rotated about their respective axes. The polyurethane film formed on the mandrels by their having been dipped into the polyurethane solution is dried in evaporation ovens at successively higher temperatures, respectively. After the pallets emerge from the last evaporation oven, they are preferably subjected to a repeat of the process just described for a second dipping of the mandrels.

After this is done, the pallets are transported to a series of stations in an air atmosphere that respectively form one or more permanent rings at the open ends of the condoms on the mandrels, apply powder and remove the condoms from the mandrels. Alternatively, a wet takeoff system can be used. The pallets of mandrels freed of condoms are washed in one station, and rinsed in another, before being transported via a staging conveyor to an inspection and redress station. After completion of the inspection and redress, the pallets and mandrels are transported to a drying oven station. After drying, the pallets and associated mandrels are ready to be passed through the chambers just described starting with the cooling chambers, for another cycle making condoms.

Because of the high flammability and explosiveness of the solvent, THF, means are provided for keeping the oxygen concentration below given levels in each of the chambers referred to by introducing $N_2$, and operating with the THF in a substantially oxygen free atmosphere. The expense of the operation is reduced by recovering THF from the atmosphere expelled from the chambers by utilizing a closed-loop system that passes through a condensing or absorption system. With this process the $N_2$ is reused, and heat exchangers are employed for extracting heat for use in the process. In this manner, through recovery of THF, $N_2$, and heat, the process is made highly economic, and environmentally friendly. Also, any imperfect polyurethane condoms can be recycled back into the system.

Since the stations in the section where the final product is removed from the mandrels, and the mandrels are cleaned, inspected, redressed, and dried, respectively, are in the ambient or air atmosphere containing oxygen, and the chambers in the section where the product is formed on the mandrels in a nitrogen and oxygen reduced atmosphere, the mandrels are passed from one section to the other via an air lock.

BRIEF DESCRIPTION OF THE DRAWINGS

Various embodiments of the present invention are shown and described herein with reference to the drawings, in which like items are identified by the same reference designation, wherein:

FIG. 22A is an enlarged view of a portion of the X-Y snapper assembly showing details of the suction nozzle assembly thereof;

FIG. 22B is a detailed view of the front of an individual suction nozzle of FIG. 22A;

FIG. 23 is a partial pictorial and partial sectional view of an individual air nipple assembly;

FIG. 24 is a top view of an air nipple of the air nipple assembly of FIG. 23;

DETAILED DESCRIPTION OF THE INVENTION

Figure 1A:
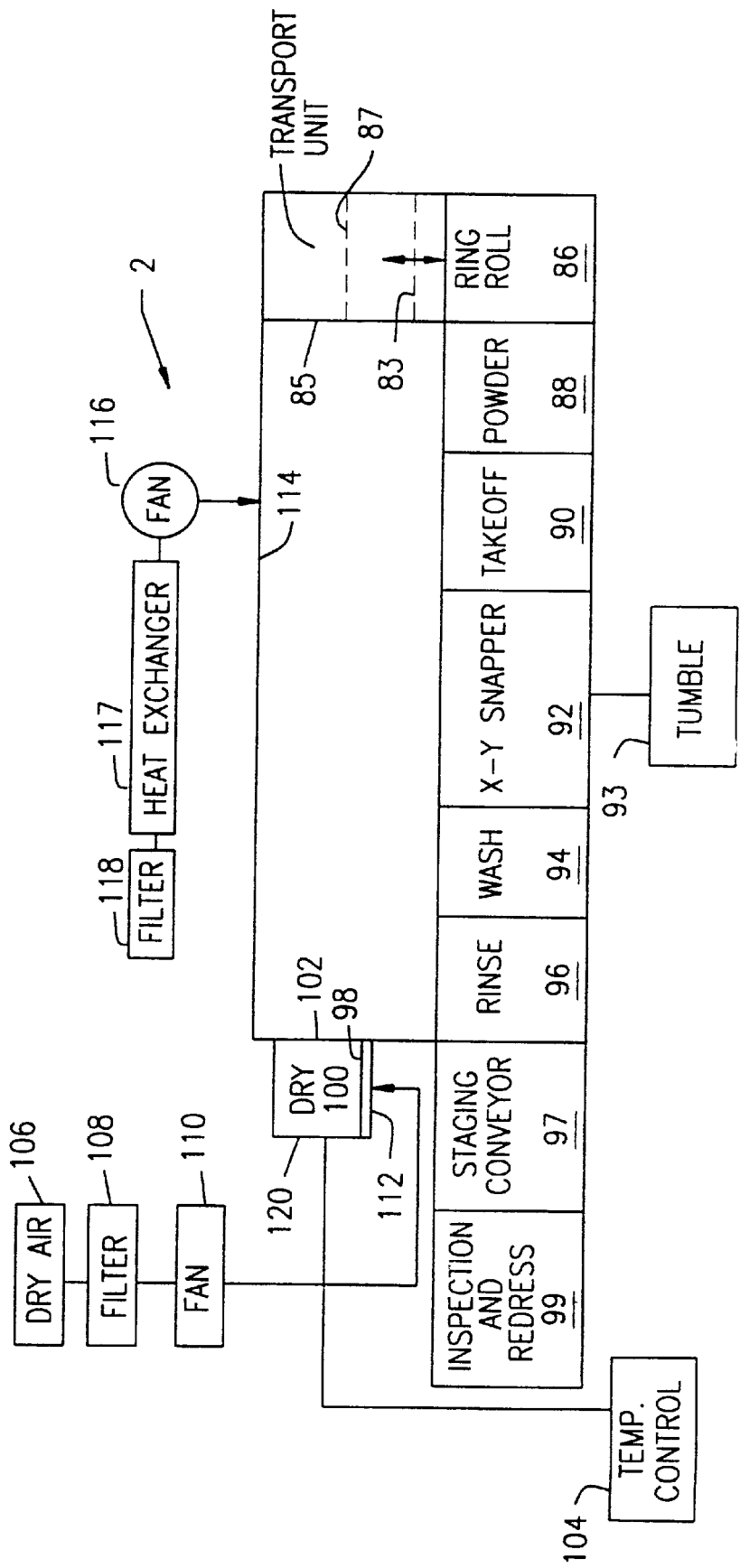
FIGS. 1A and 1B are block diagrams of the principal components of apparatus for making prophylactic devices in accordance with the invention.

The making of prophylactic devices in accordance with the method of this invention is best explained by the following description of apparatus of the invention that operates in accordance with the method. Although the method could be used to make any prophylactic device, the apparatus will be described in connection with the manufacture of condoms.

The complete method is a closed loop in which mandrels 178 (see FIGS. 4B, 4C and 5) generally shaped like condoms are carried by pallets 176 from cleaning and drying stations to be described that are in a Section 2 (see FIG. 1A) to a succession of chambers in a Section 4 (see FIG. 1B) where at least one polyurethane film is formed on the mandrels 178. Then the pallets 176 are returned to stations in the Section 2 in which the film on each mandrel 178, which now has a condom with a permanent ring formed at its open end, is powdered and removed in a dry process, or removed using a wet process. The mandrels 178 are then cleaned, inspected and redressed, if necessary to replace a defective mandrel 178 or strip-off a condom not previously removed. The mandrels 178 are then ready for reuse in producing condoms.

As will become clear, the Section 2 where the mandrels 178 are cleaned and the condoms removed contains an air atmosphere, and the Section 4 where the film is formed on the mandrels contains an inert atmosphere including the solvent used in the film forming process. Preferably, the solvent is THF. The reason is that through experiments, the present inventor found THP to have excellent solubility for polyurethane, relative to other solvents, and it is easily removed from polyurethane. It is important to insure that all solvent is removed from the condom. Because of the explosive nature of THF, the infiltration of air from the Section 2 to the Section 4 must be minimized, and because of the flammability of the THF, its infiltration from the Section 4 to the Section 2 must be minimized even though pallets 176 of mandrels 178 are passed in both directions between the two sections. Minimizing these infiltrations is accomplished by an air lock 6 (see FIG. 1B) between the cleaning and product removal Section 2 and the film forming Section 4.

Note that the present invention provides a system that is capable of manufacturing prophylactic devices consisting of natural and synthetic elastomers. For example, as indicated polyurethane is such as material, as is latex. Other water-based polymers may 1 include nitrite rubber, neoprene rubber, SBS rubber emulsion, polyvinyl alcohols, polyvinyl acetate, polyacrylates, polyethylene glycols, and alkyl cellulose. Other solvent based polymers may include polyisoprene, SBS rubber, silicone rubber, polyolefms, polyamides, polyesters, PVC, polymethylmethacrylate, polyacrylates, polyacetals, polycarbonates, polycaprolactams, and halogenated polymers. Note that the water-based polymer examples are also soluble in solvents. Other polymer materials may also include copolymers, terpolymers, block polymers, and so forth.

Figure 1B:
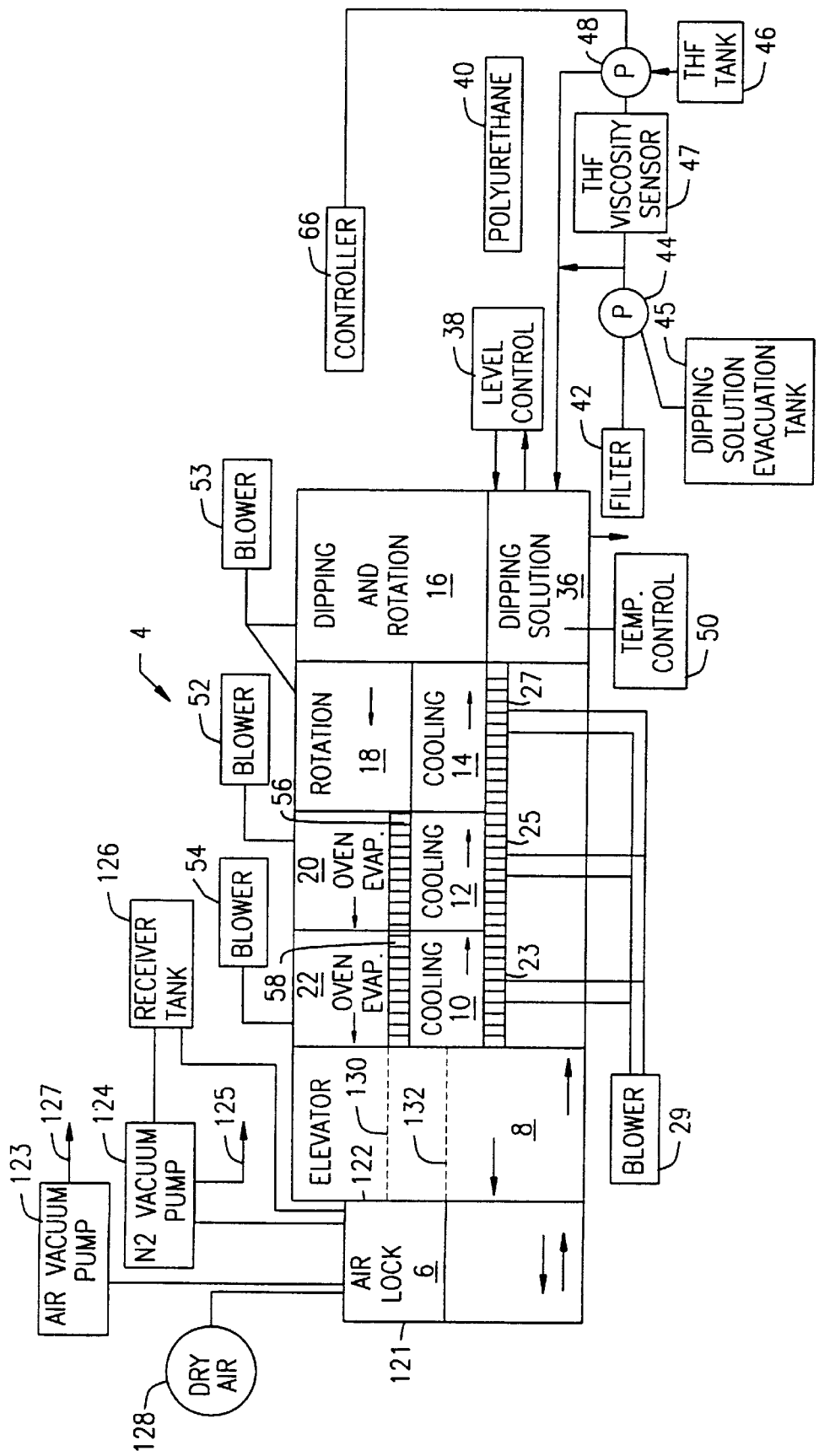

The following description of the operation of the system of FIG. 1B starts with the transfer of a pallet 176 of mandrels 178 from an airlock 6 to an elevator chamber 8. In a manner to be explained in the discussion of FIGS. 1B, 1C, 1D and 1E, the pallet 176 is transported so as to spend successive periods of time isolated in a first cooling chamber 10, a second cooling chamber 12, a third cooling chamber 14, a dipping chamber 16 where the mandrels 178 are coated with a polyurethane film, a rotation chamber 18, a first evaporation oven chamber 20, a second evaporation oven chamber 22 and back to the elevator chamber 8. At this point, one polyurethane film has been deposited on the mandrels 178 so that the pallet 176 could be passed back through the air lock 6 into the Section 2 where the condoms are removed and the mandrels 178 are cleaned in preparation for another trip through the condom forming Section 4 as just described. Preferably, however, a second polyurethane film is formed on the first film by repeating the trip just described, in which event the pallet 176 is conveyed by an elevator in the elevator chamber 8 back to the first cooling chamber 10. In the same manner layers of more than two films can be formed. Through use of multiple dip capabilities, the present invention provides relative to the prior art faster overall cycle times and minimizes defects. In certain product applications more than two films may be formed on each mandrel 178.

A detailed description of the apparatus and operations carried out in the various chambers of the film forming Section 4 is as follows. In order to ensure that the mandrels 178 are smooth and can be readily cleaned and stripped they are made of non-porous material such as glass. In an alternative embodiment, the mandrels 178 can be frosted or etched to enhance removal of the film. Note that the mandrels can also be made from any other suitable material, not limited to glass. When they enter the first cooling chamber 10 for the first time, they will be hot because of having been passed through a drying station 100 (see FIG. 1A) in the Section 2, and when they enter it a second time, they are hot because of having come from the second evaporation oven chamber 22. Because the temperature of the polyurethane solution into which the mandrels 178 will be dipped in the dipping unit chamber 16 in either case is kept at about 50° F. to 70° F., there is a chance that the mandrels 178 will crack, and/or excessive outgassing of the solvent will occur, if the mandrels 178 are at a temperature higher than about 58° F. In order to prevent this from occurring, the pallets 176 of mandrels 178 spend successive periods of time in the cooling chambers 10, 12 and 14 that are preferably at successively lower temperatures. Means not shown such as conventional heat exchanger configurations through which water or refrigerant of a proper temperature is circulated are provided for maintaining the cooling chambers 10, 12 and 14, respectively, at appropriate temperatures between the temperature of the drying station and the temperature of the dipping chamber 16, which is at about 70° F. An adjustable high velocity and even flow of air is maintained in the cooling chambers 10, 12 and 14, by circulation of air in them through respective honeycombed structures 23, 25 and 27 in their bottoms with blowers 29. Note that the air flow is adjustable throughout Section 4.

Figure 4A:
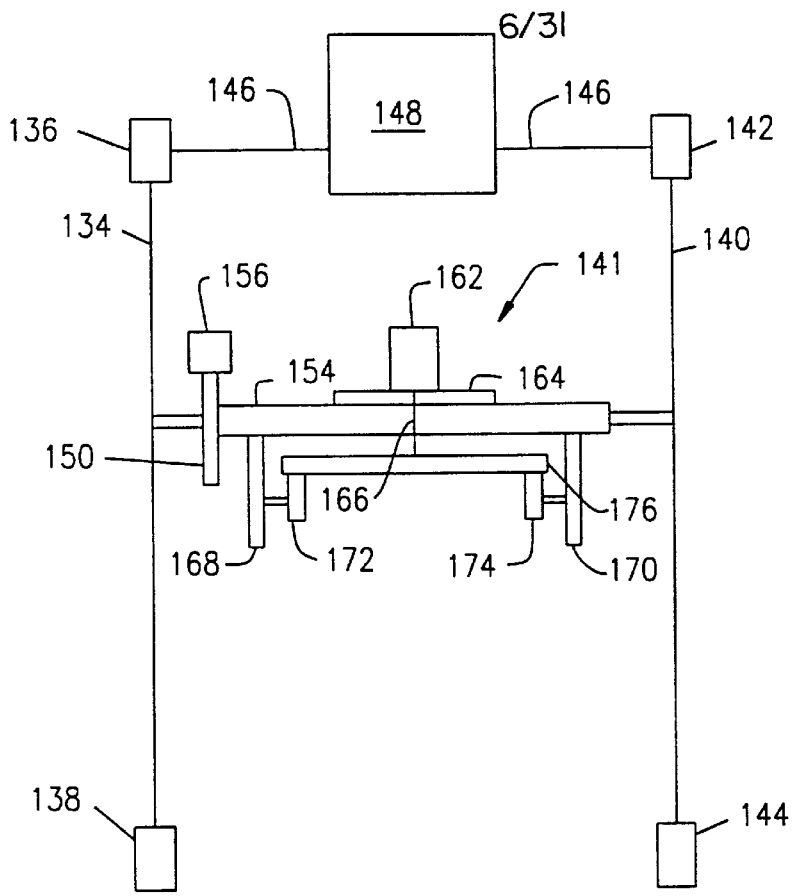
FIG. 4A illustrates an elevator and mechanism for rotating the pallets as well as the mandrels.
Figure 4B:
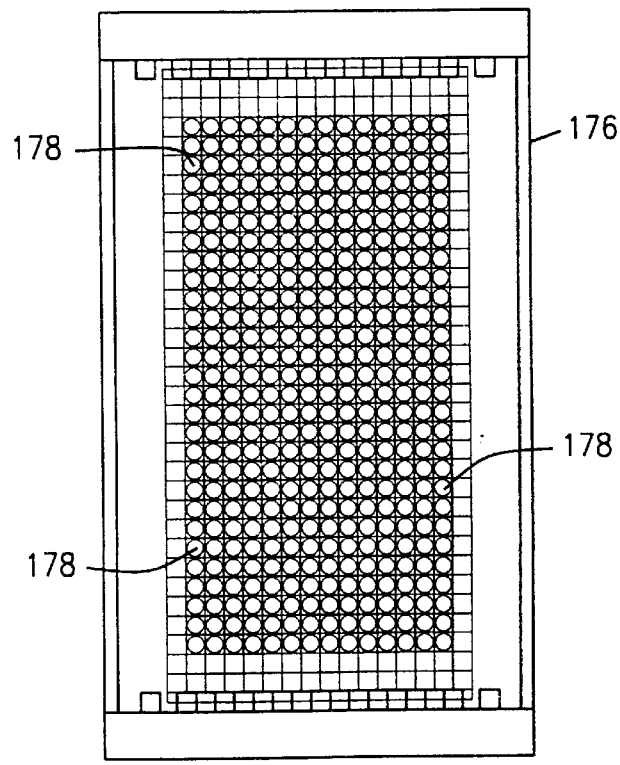
FIG. 4B is a bottom view of a pallet carrying mandrels.

When a pallet 176 is passed from the last cooling chamber 14 into the dipping chamber 16, it engages a dual axis robotic mechanism that is capable of vertical and rotational movement, simplistically shown in FIG. 4A, that dips the pallet 176 at carefully controlled rates of speed and without vibration into and out of a reservoir 36 of polyurethane material dissolved in THF.

A level control mechanism 38 senses when the level of the polyurethane solution in the reservoir 36 drops below a given level and pumps more polyurethane solution into the reservoir 36 from a tank 40. Circulation of the solution so as to keep it homogeneous and free from particulate matter is achieved by a filter 42 and a pump 44. In order to obtain consistent results, the viscosity of the solution in the reservoir 36 is kept constant by sensing the viscosity in the circulation loop with a viscosity sensor 47 and causing an appropriate amount of THF to be injected from a tank 46 into the circulation line with a pump 48. It is also necessary to maintain the temperatures of the polyurethane solution constant with a suitable temperature control means 50. The temperature of the polyurethane solution is typically 50° F. to 70° F., with the concentration of THF maintained at 3% to 7% in the atmosphere of chambers 16 and 18.

Both uniformity and the profile of the thickness of a film of polyurethane solution on the mandrels 178 is significantly improved by rotating the pallet 176 about a horizontal axis by as much as 360°. Whereas the mandrels 178 can also be rotated about their respective axes both in a clockwise and counterclockwise direction in the dipping reservoir chamber 16, chamber 18, and evaporation ovens 20 and 22. This is preferably done simultaneously in the dipping chamber 16 and rotation chamber 18 along with rotation of the pallet 176. The axial mandrel 178 rotation is controlled at speeds up to one hundred rpm, and the 360° pallet 176 rotation is controlled to speeds up to six rpm.

Evaporation of the THF solvent in the film deposited on the mandrels 178 in the dipping solution reservoir chamber 36 so as to form polyurethane condoms on the mandrels is achieved in the dipping and rotation chamber 16, rotation chamber 18, and evaporation oven chambers 20 and 22. Circulating air for the oven chambers 20 and 22 is respectively provided by blowers 52 and 54. Air circulation in chambers 16 and 18 is provided by a common blower 53. Evenly controlled flow is achieved by causing the air to flow downwardly along the outside surfaces of the oven chambers 20, 22 which are equipped with heat exchangers (not shown), and upwardly through their center through honeycombed structures 56 and 58, respectively.

Accordingly, in the illustrated embodiments of the invention provided herein evaporation is used to drive THF from the film. However, with polyurethane film formula structures water quenching or stripping can also be used rather than evaporation to remove the THF from the film formed.

Figure 3:
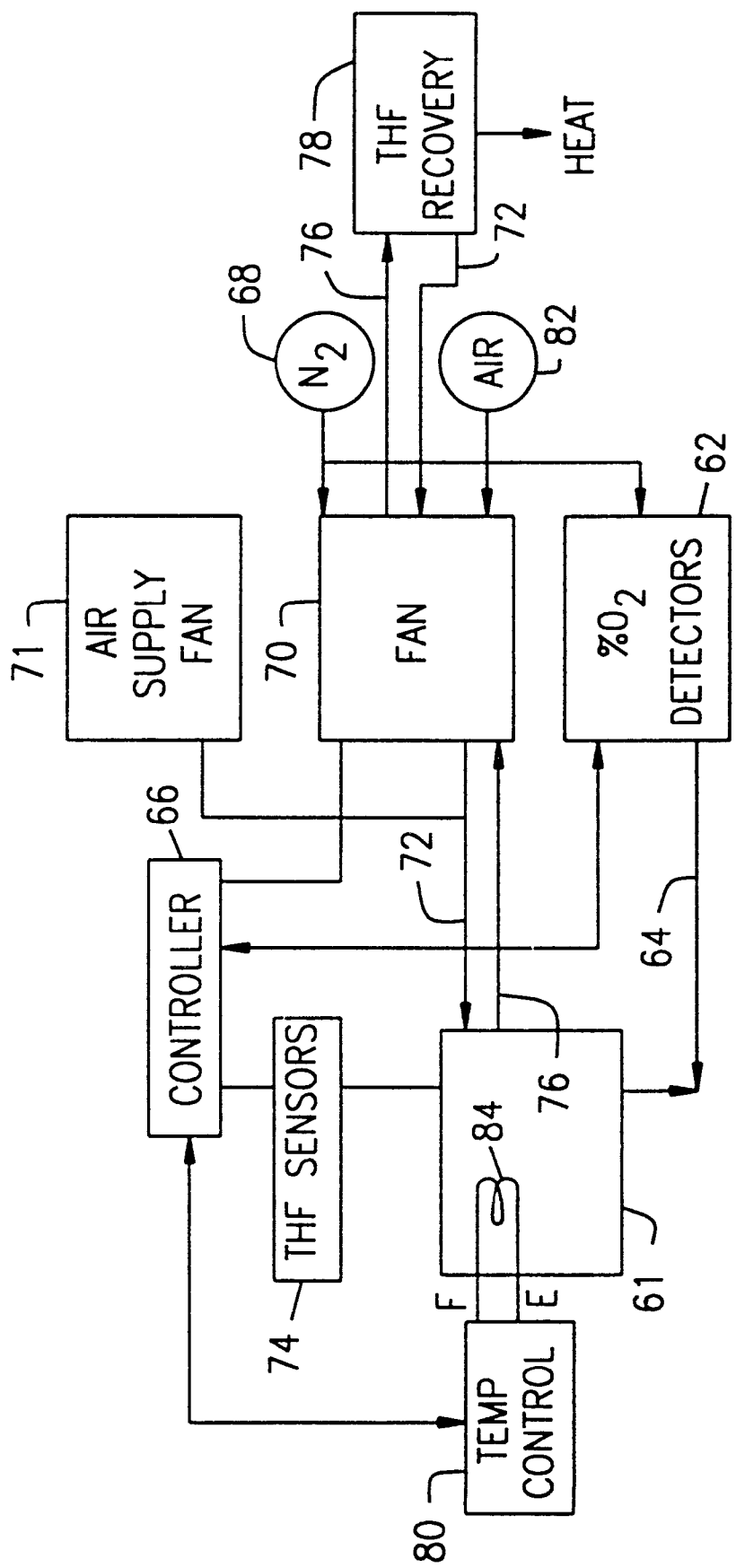
FIG. 3 is a block diagram of apparatus used to control the temperature, percent $O_2$ and percent solvent in various chambers of the apparatus of FIG. 1.

For optimum operation, the temperature and THF concentration in the chambers 8, 10, 12, 14, 16, 18, 20 and 22 must be maintained within appropriate ranges, and for safe operation, the concentration of $O_2$ in these chambers is maintained at sufficiently low levels. In order to reduce cost, the solvent THF is recovered. One way of performing these functions is to use apparatus such as shown in FIG. 3 for each chamber of film forming Section 4, herein designated as 61, for representing each independent chamber. All of the aforesaid temperatures are interdependent, along with the dipping speed, dipping times, rotational speeds of mandrels 178, withdrawal and insertion rates, angular positions, velocities, and so forth. For example, in one embodiment oven 20 is maintained at 120° F., oven 22 at 140° F., cooling station 10 at 40° F., cooling station 12 at 42° F., cooling station 14 at 41 ° F., and dipping and rotation stations 16 and 18 at 60° F.

The required low concentration of $O_2$ is secured by using detectors 62 (see FIG. 3) to constantly sample gas from the chamber 61 via tubes 64 and provide an indication to a controller 66 of the concentration of $O_2$. When an indication of too high a concentration occurs, the controller 66 causes an inert gas such as $N_2$ from a source 68 to be introduced into the chamber 61 via a tube 72 until a sufficiently low concentration of $O_2$ is indicated. This is the source of $N_2$ that will be found in all the chambers of the film forming Section 4. Note that the $O_2$ detection systems are redundant throughout the present system.

The following table suggests the maximum concentrations of the solvent, THF, that preferably should be maintained in the various chambers. The maximum values attainable in the below listed zones 3 and 4 (see Table 1) may be limited as necessary to prevent solvent condensation on equipment within each zone.

TABLE 1

| ZONE NO. | ZONE | SOLVENT CONCENTRATION |
| --- | --- | --- |
| (1) | Elevator chamber 8 | Less than 1% THF |
| (2) | Cooling chambers 10, 12, 14 | Less than 1% THF |

TABLE 1-continued

| ZONE NO. | ZONE | SOLVENT CONCENTRATION |
| --- | --- | --- |
| (3) | Dipping chamber 16 and pallet rotation chamber 18 | 1–11% THF |
| (4) | Solvent evaporation oven 20 | 1–11% THF |
| (5) | Solvent evaporation oven 22 | Less than 2% THF |

In order to establish and maintain the THF concentrations set forth in Table 1, solvent sensors 74 (see FIG. 3) provide signals to the controller 66 indicative of the THF concentration in the chamber 61. The controller 66 modulates return valves (not shown) from the recovery system and controls $N_2$ return from the source 78 into the chamber 61 via the tubes 72 until the THF concentration is reduced to or maintained at the the desired level. The gasses expelled from the chamber 61 via a tube 76 are transported to a means 78 for recovering the THF, which may be a BRAYCYCE® solvent recovery system, for example. The THF recovered is delivered to the tank 46 of FIG. 1B. The heat generated by the process in the recovery system is made available for heating fluid flowing in the heat exchangers, not shown, of the evaporation oven chambers 20 and 22, and drying oven 100, chamber 114, wash tank 94, and rinse tank 96. Note that solvent laden $N_2$ from the process is transferred from chamber 61 to THF recovery source 78. The solvent is condensed out, and the process $N_2$ is transported back to chamber 61 via tubes 72.

If it is desired to gain access to the film forming Section 4, the controller 66 operates pump 44 (see FIG. 1B) to pump dipping solution from reservoir 36 into evacuation tank 45. The atmosphere of Section 4 is then recirculated through the solvent recovery system 78 until solvent or THF levels are reduced to acceptable levels. Next, filtered atmospheric air is introduced via air supply fan 71 (see FIG. 3) into Section 4 to bring oxygen levels to a safe level for human entry. This is done for all chambers of Section 4.

The temperature of a chamber generally designated as 61 is controlled by sensing the temperature of the chamber 61 with a means in a temperature control 80 that sends a signal to the controller 66. As the temperature varies about a desired value, the controller 66 causes the temperature control 80 to vary the amount of cooling/heating fluid flowing through heat exchangers 84 that are in the air recirculation stream of chamber 61, that is in each chamber of Section 4, respectively.

Section 2

When a pallet 176 of mandrels 178 has been fully processed in the film forming Section 4, it is transferred from the elevator station 8 to the air lock 6 and is then transferred directly to the lower level 83 (see FIG. 1A) of a robotic transport unit 85. The transport unit 85 is successively positioned over stations 86, 88, 90, 94 and 96. At each station the transport unit lower level 83 is lowered so that the function of the station can be carried out.

In FIG. 1A, the transport unit 85 is shown as being in registration with the station 86 wherein the open ends of the condoms on the mandrels are rolled down a short distance to form rings. The rings are permanent, and can be made so in different ways known in the art other than by rolling. For example, by gluing, bonding, sewing, or extruding a ring on the condom. However, in this example, as indicated, the ring is formed by partially rolling the open end of the unpowdered condom to form the ring, which becomes permanent because the material bonds to itself at this time. The condoms are powdered in the station 88 and removed from the mandrels 178 in the station 90, and via the X-Y snapper station 92 the condoms are removed from the takeoff station 90. The condoms are collected and placed into a tumbler apparatus at station 93 to permit the condom material the additional time necessary to obtain sufficient crystallization for obtaining winkle free condoms. The tumbler apparatus (not shown) can be clothes dryer or washer modified for tumbling the condoms at ambient temperature. The mandrels 178 are washed in the station 94 by soaking them in an ultrasonically activated cleaning solution or R.O (reverse osmosis) water, and rinsed in the station 96 with hot R.O water. R.O water is used to avoid environmentally sensitive discharges as would be experienced with deionized water systems and regeneration of the same. Although R.O water is preferred for use in the cleaning process, tap and/or deionized water can also be used.

The pallet 176 of rinsed mandrels 178 is moved onto a staging conveyor 97 which conveys the pallet 176 to an inspection and redress station 99. The mandrels 178 that may be defective are replaced, and condoms or condom fragments if any are removed from the mandrels 178. The redressed pallet 176 is then conveyed from the redress station 99 to the drying oven 100, and then to level 87 of the transport unit 85. Note that the inspection and redress station 99 can also be used to change a pallet 176 of mandrels 178 to make a different style of condom or product, or remove a defective pallet 176 on the fly.

The temperature in the oven 100 is regulated by a temperature controller section 104 included in controller, in this example, preferably between 160° and 180° F. Dry make-up air is drawn from a source 106 and through a filter 108 by fans 110 and with recirculated air directed upwardly through a honeycomb structure 112 just below the bottom 98 of the oven 100. In order to obtain consistent drying, the relative humidity in the oven 100 is controlled by automatic modulation of the exhaust air flow, by measuring the humidity and opening an exhaust damper to expel moisture laden air. The space over the stations 86, 88, 90, 92, 94 and 96 is enclosed as indicated at 114, and the temperature therein is removed by forced ventilation with a fan 116 that draws air through a filter 118, and through heat exchanger 117, and expelled by two exhaust fans (not shown) on each end of the chamber 114.

The transport unit 85 removes pallet 176 of the dried mandrels 178 from oven 100 on its upper level 87, and transports pallet 176 to air lock 6, for reintroduction into Section 4, after removing a pallet 176 from air lock 6 to level 83 of the transport unit 85. The pallet 176 and associated mandrels 178 are then moved through the various stations of Section 4 to form condoms on the mandrels 178, as previously described.

When the system of FIGS. 1A and 1B is in normal operation, twelve pallets 176 are being processed at various stations and chambers. In other embodiments, more or less pallets 176 may be provided. A pallet 176 that is in the drying oven 100 can be replaced or accessed if necessary by opening a door 120 without interrupting the operation of the system. This is a less preferred access than that provided by the inspection and redress station 99.

Figure 2:
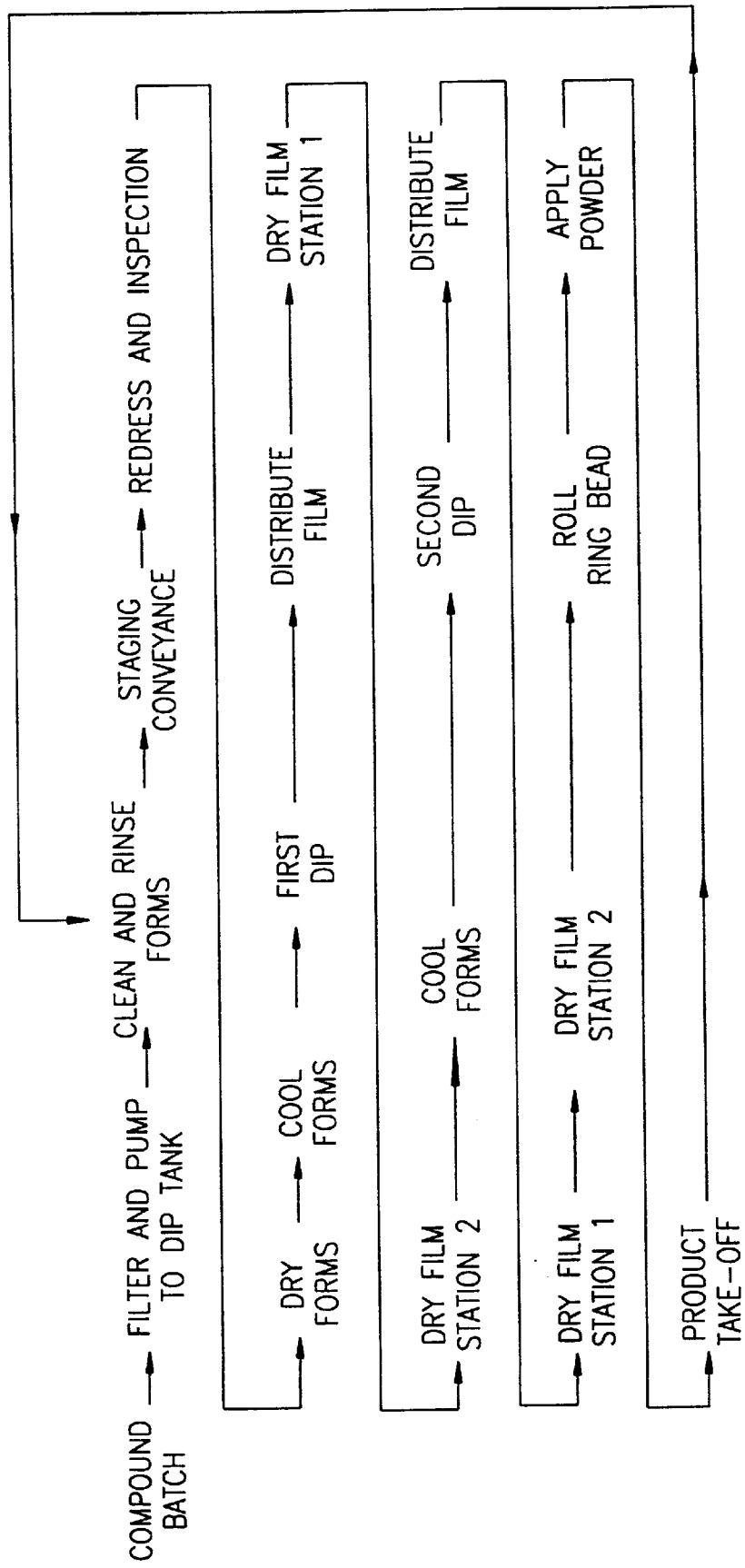
FIG. 2 is a flowchart of the steps in making a prophylactic device in accordance with the invention.

The sequence of operation of the system of FIG. 1A as set forth in FIG. 2 and in the Table 2 below, is controlled by the controller 66. Table 2 shows a time sequence of events occurring in FIG. 1B, and is a practical example, not meant to be limiting. Because this system is programmable, and fully multitasking, flexibility is provided to adapt to other processes and/or cycle times with minimum physical modifications.

TABLE 2

| Event | Preferred (In Seconds) | Range (In Seconds) |
|---|---|---|
| (1) Transfer from drying oven 100 to air lock 6 | 40 | 30–50 |
| (2) Air lock 6 cycle to purge air and introduce nitrogen | 80 | 60–120 |
| (3) Transfer from air lock to cooling chamber 10 | 10 | 7–20 |
| (4) To cooling chamber 10 | 90 | 80–120 |
| (5) To cooling chamber 12 | 90 | 80–120 |
| (6) To cooling chamber 14 | 90 | 80–120 |
| (7) First dip in dipping unit chamber 16 | 85 | 70–120 |
| (8) Rotate and distribute film in rotation chamber 18 | 70 | 60–120 |
| (9) Dry film in oven chamber 20 | 90 | 80–120 |
| (10) Dry film in oven chamber 22 | 90 | 80–120 |
| (11) Transfer in elevator chamber 8 to air cooling chamber 10 | 20 | 15–25 |
| (12) To cooling chamber 10 | 90 | 80–120 |
| (13) To cooling chamber 12 | 90 | 80–120 |
| (14) To cooling chamber 14 | 90 | 80–120 |
| (15) Second dip in dipping chamber 16 | 85 | 70–120 |
| (16) Rotate and distribute film in chambers 16 and 18 | 70 | 60–120 |
| (17) Dry film in oven chamber 20 | 90 | 80–120 |
| (18) Dry film in oven chamber 22 | 90 | 80–120 |
| (19) Transfer to air lock chamber 6 | 20 | 15–25 |
| (20) Air lock 6 opened to air | 80 | 60–120 |
| (21) Discharge from air lock 6 onto transport unit 95 | 10 | 7–20 |
| (22) Form ring roll, station 86, and transfer to powder station 88 | 30 | 20–80 |
| (23) Powder application and transfer to takeoff station 90 | 20 | 10–80 |
| (24) X–Y snapper 92 removal of finished product from takeoff station 90, and transfer of mandrels 178 to wash station 94 | 30 | 20–120 |
| (25) Wash mandrels 178 in station 94 and transfer to rinse station 96 | 25 | 15–45 |
| (26) Rinse in station 96 | 25 | 15–45 |
| (27) Transfer to staging conveyor 97 for conveyance to inspection and redress station 99 | 10 | 7–15 |
| (28) Redress | 180 | 120–240 |
| (29) Transfer to drying oven 100 and transport unit 95 | 10 | 7–15 |
| (30) Air dry mandrels 178 in drying oven 100 | 180 | 160–240 |
| PREFERRED GRAND TOTAL . . . 1,980 SEC. (33 min or 11 pallets × min./cycle) | | |

Operation of Air Lock

The air lock 6, FIG. 1B, is provided with what is called an air side door 121 opening into Section 2, which, it will be recalled has normal air atmosphere. Air lock 6 also includes a nitrogen side door 122 opening into the elevator chamber 8 of Section 4, which, as previously mentioned can have a nitrogen or other inert atmosphere with a slight concentration of THF.

A pallet 176 of clean mandrels 178 from the Section 2 is passed into the film forming Section 4 by opening the air side door 121, moving the pallet 176 into the air lock 6 and closing the air side door 121, the nitrogen side door 122 being closed. A vacuum pump 123 pumps the air lock 6 down to a deep vacuum that is preferably less than 12 torr, which is less than 1% of the average atmospheric pressure, in order to minimize air (oxygen) infiltration into the Section 4. Air from the pump 123 exits at 127. The vacuum is then broken by permitting nitrogen to flow into the air lock 6 from a receiver tank 126 or any suitable source, thereby equalizing its pressure with that in Section 4. The nitrogen side door 122 is then opened and the pallet 176 is passed into an elevator mechanism (not shown) in the elevator chamber 8.

A pallet 176 can be passed from the film forming Section 4 to the Section 2 by passing it from the elevator section 8 into the air lock 6. The nitrogen side door 122 is then closed, and vacuum pump 124 pumps the air lock 6 to less than 12 torr vacuum, but preferably sends its exhaust into a receiver tank 126 rather than existing into the atmosphere via outlet 125. The vacuum is broken by connecting the air lock 6 to a source 128 of dry filtered air, the air side door 121 is opened and the pallet 176 is passed onto the lower level 83 of the transfer or transport unit 85. The purpose of the receiver tank 126 is to conserve nitrogen because it can be the source of nitrogen when vacuum in the air lock 6 is to be broken by admitting nitrogen into it.

Elevator

Figure 1C:
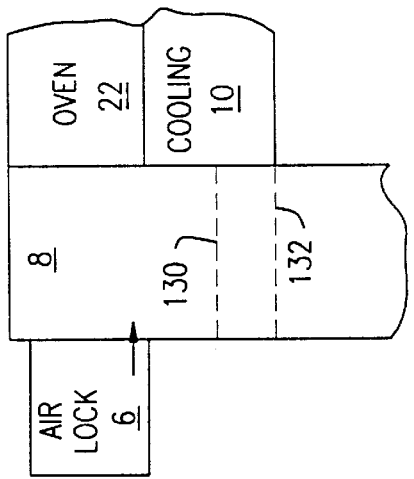
FIGS. 1C, 1D, 1E, and 1F respectively illustrates the manner in which the elevator shown in FIG. 1A operates to position pallets for transfer between different parts of the apparatus.
Figure 1D:
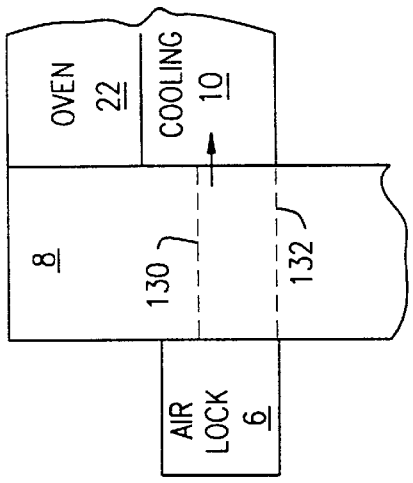
Figure 1E:
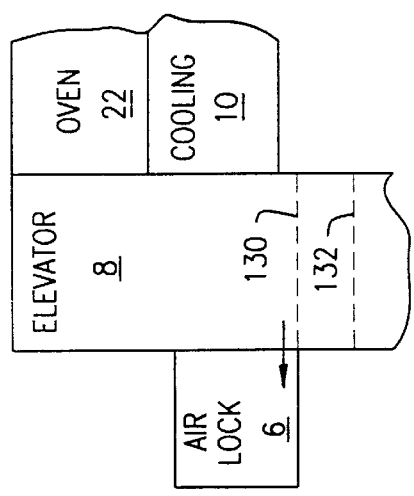
Figure 1F:
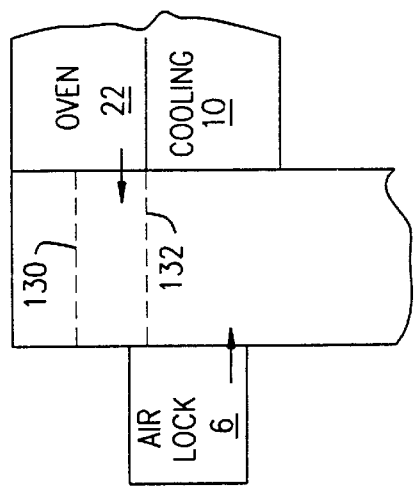

The elevator in the elevator chamber 8, not shown in detail in FIG. 1B, has two shelves 130 and 132 that are spaced by half the equal heights of the air lock 6, the evacuation oven chamber 22 and the cooling chamber 10. When the shelves 130 and 132 are in the positions shown in FIG. 1B, a finished pallet 176 can be moved from the oven chamber 22 onto the elevator shelf 130, and a new clean pallet 176 can be moved from the air lock 6 onto the shelf 132. In FIG. 1C, the finished pallet 176 can be moved from the shelf 130 to the air lock 6. In FIG. 1D, the new pallet 176 can be moved from the shelf 132 to the cooling chamber 10. If a pallet 176 is to be recycled so as to form a second polyurethane film on the mandrels 178, the shelf 130 is placed even with the bottom of the oven chamber 22 (see FIG. 1E), and the pallet 176 in the oven chamber 22 is moved onto it. Then the elevator lowers the shelf 130 to the bottom of the cooling chamber 10 (see FIG. 1F) so that the pallet 176 can be placed in that chamber a second time. Note that FIGS. 1B through 1F are not drawn to scale or in perspective, and are meant for purposes of illustration only.

Rotation

In each of the dipping unit chambers 16 and rotation chamber 18, the dipping solution reservoir 36, and evaporation oven 20, the mandrels 178 are rotated about their axes. In chambers 16 and 18 the mandrels 178, as well as the pallets 176 in which they are mounted are rotated about an axis in their planes. One way of achieving these rotations in the dipping chamber 16 as well as performing the dipping function is illustrated in FIG. 4A. These rotations produce walls of desired thickness profiles in the prophylactic devices formed on the mandrels 178.

In FIG. 4A, a chain 134 is mounted about upper and lower sets of sprockets 136 and 138, and a chain 140 is mounted about upper and lower sets of sprockets 142 and 144. The sprockets 136, 138, 142 and 144 are mounted on the walls of the chamber 16 for moving a robot 141 in a vertical plane, and the shafts plans 146, driven by an electric motor 148 that is also mounted on a wall of chamber 16 is connected between the centers of the sprocket sets 136 and 142 so as to be able to rotate them.

Gear 150 is secured to the elevator platform 154 in such manner that it does not rotate. The elevator platform 154 is mounted for rotation about the center of gear 150 by a chain about gear 150 driven by a motor 156 and a gear set (not shown). In this example, the motor 162 is affixed to the platform 154. The motor 162 has a vertical shaft 166. Motor 164 is also affixed to the platform 154 and turns roller sets 172 and 174. Projections 168 and 170 extend downwardly from the platform 154 and have powered roller sets 172 and 174, respectively, driven by motor 164, mounted on them. A pallet 176 that is shown as being mounted on the rollers 172 and 174 has mandrels 178 extending downwardly from it as shown in the bottom view of FIG. 4B. As will be described in connection with FIG. 4C, gears 208 are coaxially mounted on the upper ends of the mandrels 178 that are intermeshed in such manner that rotation of one gear 208 rotates all the others. One gear 208 is rotated by engagement with the shaft 166 of the motor 162. In order to permit the pallet 176 to be moved in and out of the chamber 16, it is necessary that provision be made for vertical movement of the shaft 166. Rotation of the gear sets 136, 138, 142 and 144 by operation of the motor 148 raises or lowers the entire assembly 141 between chains 134 and 140. The assembly 141 is lowered when the mandrels 178 are to be dipped into the dipping solution reservoir 36, and is raised when the pallet 176 and mandrels 178 are to be rotated. It is also raised when a pallet 176 and its attached mandrels 178 are to be transferred to the rotation chamber 18.

When the pallet 176 is in position, it can be raised or lowered by raising and lowering the platform 154 by operation of the motor 148. Rotation of the pallet 176 about an horizontal axis is effected by turning motor 156 and its gear set in a chain about gear 150, and also concurrently or independently rotation of the mandrels 178 about their respective axes is achieved by operation of the motor 162.

The structure for rotating the pallet 176 and the mandrels 178 when the pallet 176 is in the rotation chamber 18 is the same as in FIG. 4A, but no vertical movement is required so that the motor 148, the sprockets 136, 138, 142 and 144 and the chains 134 and 140 are not required.

Figure 4C:
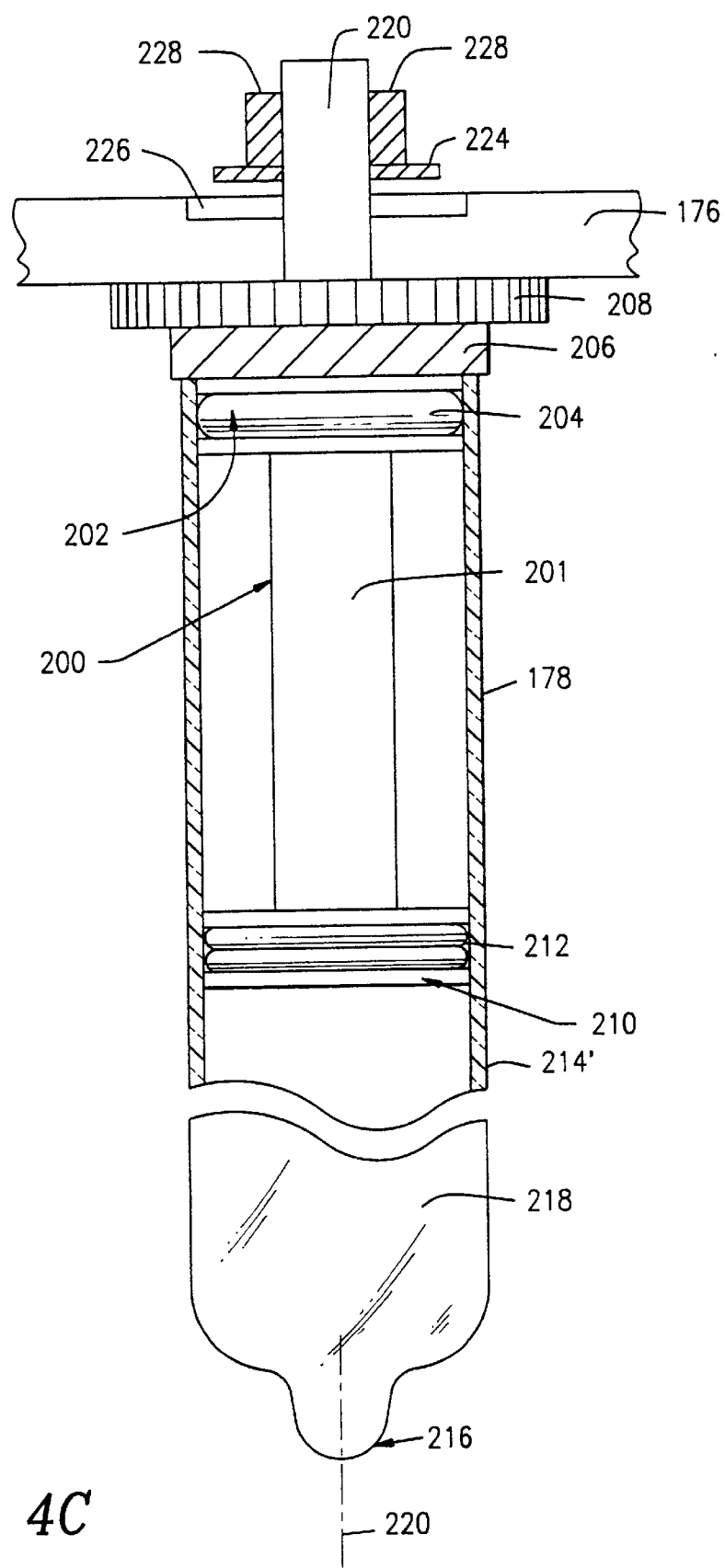
FIG. 4C is pictorial and side elevational view of a glass mandrel with an electrically conductive coating, as mounted on a mandrel holder for one embodiment of the invention.
Figure 4D:
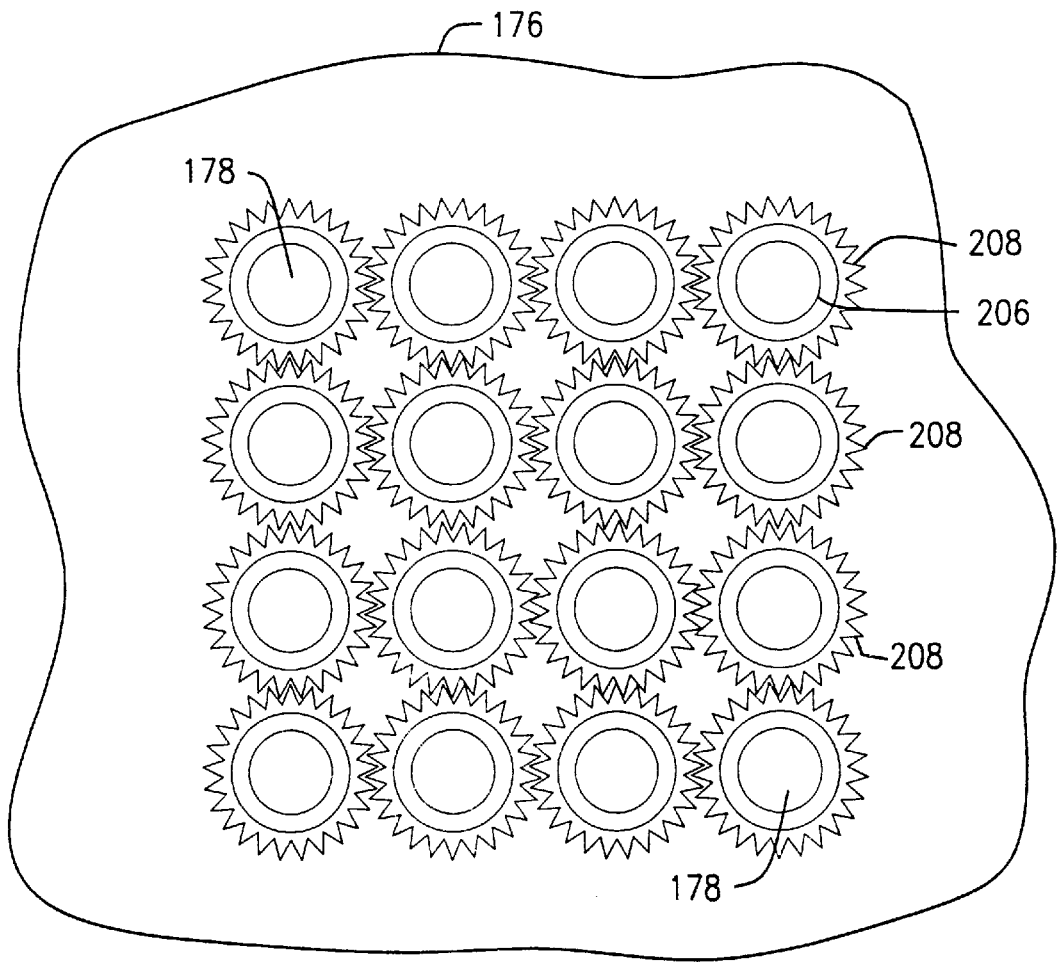
FIG. 4D is a bottom view of a pallet showing intermeshed gears for rotating the mandrels about their respective axes.

In FIG. 4C, a mandrel holder 200, all in one piece, that is made of material that does not react with the solvent, has a groove 202 molded and/or machined into it in which an O-ring 204 is seated. In this example, a gear section 208 is coupled via a step-down hub 206 to the groove section 202. A central shaft 201 is positioned between groove section 202 and a similar groove section 210 on which an X-ring 212 is retained. A hollow glass mandrel 178 fits over and is held by the O-rings 204 and 212. One end of the mandrel 178 is preferably shaped like a nipple 216. After the films are formed on the glass mandrel 178 in the processing Section 4 of FIG. 1B, they are coated with silica powder in the powder station 88 of FIG. 1A. Typically the powder size is about 25 to 40 microns, and is charged at 20,000 to 30,000 volts. The glass mandrel 178 is provided with a conductive coating 218 that is connected via an electrical conductive O-ring 204 to a source of reference potential, such as ground so as to create an electrostatic field that attracts the powder and increases its adherence to the film, in this example. This electrical connection is provided by an electrically conductive brush (not shown) connected between O-ring 204 and shaft 220.

Each mandrel 178 assembly just described is attached to the pallet 176 by a shaft 220 that projects from the center of the gear 208 and through a cylindrical bearing 226. A washer 224 is mounted on the shaft 220 at the side of the pallet 176 that is opposite to the gear 208 and engages a bearing 226. A retention nut 228 on the shaft 220 abuts against washer 224.

Rotation of the mandrel 178 assemblies about the axis 220 is achieved by engaging their gears 208 as illustrated in FIG.

4D and connecting the shaft 166 of the motor 162 to a central one of gears 208 to act as a drive gear. When shaft 166 is engaged in a socket (not shown) of the central gear 208, and with shaft 166 rotating, each adjacent pair of the gears 208 rotate in opposite directions.

Figure 5:
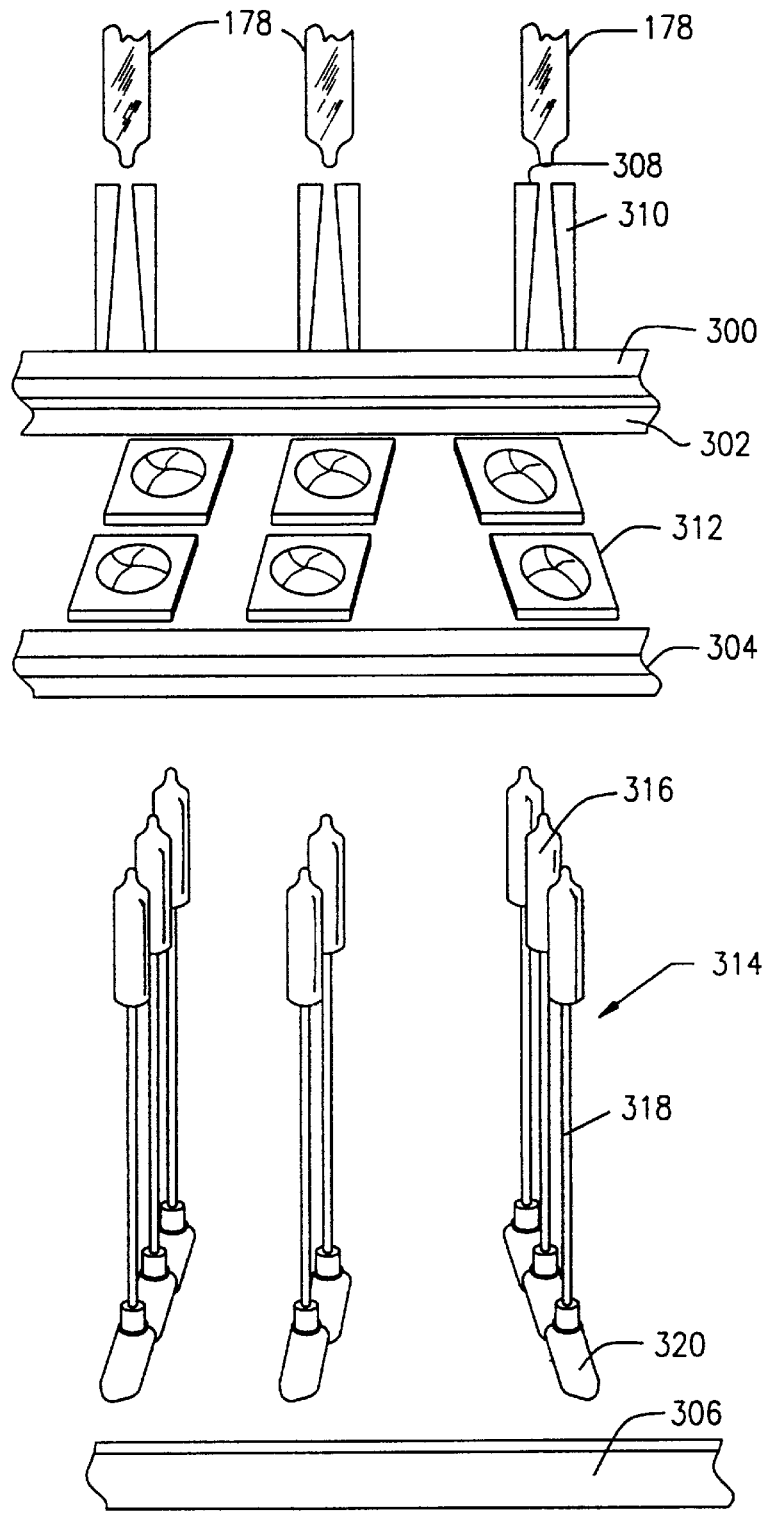
FIG. 5 is a partial pictorial view of a takeoff station for one embodiment of the invention.

The details of the apparatus associated with the takeoff station 90, and with the X-Y snapper station 92, will now be described with reference to FIGS. 5 through 27B. In general terms, the takeoff station 90 includes three main subassemblies. With reference to FIG. 5, in a simplified view of the subassemblies located below a plurality of mandrels 178 projecting from a pallet 176 retained by transport unit 85, the first subassembly includes a top shoe shifting plate 300 positioned over a bottom shoe shifting plate 302. The top shoe shifting plate 300 includes a plurality of top plate shoes or right-hand shoes 310, and the bottom shoe shifting plate includes a plurality of bottom plate shoes or left-hand shoes 308 mounted to it, as will be described in greater detail below. Each right-hand shoe 310 is paired with an individual left-hand shoe 308. Located immediately below the bottom shoe shifting plate 302 is a second subassembly that includes an insert table 304 upon which are mounted a plurality of takeoff inserts 312. The third subassembly is located below the insert table 304, and includes an air nipple table 306 upon which are mounted a plurality of air nipple assemblies 314. Each air nipple assembly 314 includes an air connector assembly 320 secured to the air nipple table 306, and vertically oriented tubing 318 projecting upward from the air connector assembly 320. An air nipple 316 is mounted at the top of each of the tubes 318, as shown. Each of the air nipples 316 are associated with an individual one of the takeoff inserts 312 and individual one of a pair of shoes 308 and 310.

Figure 6:
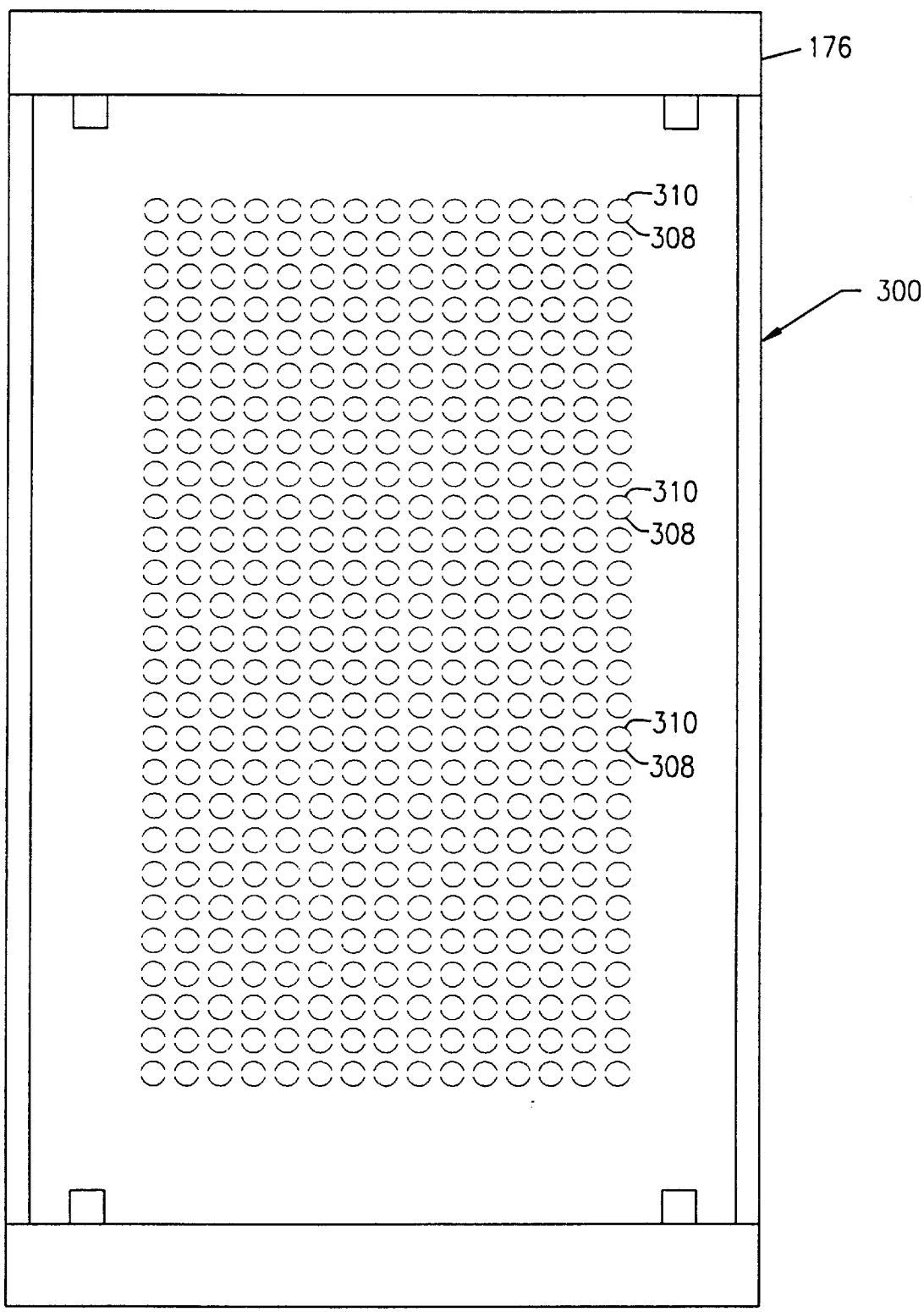
FIG. 6 is a top view within the takeoff station of FIG. 5, looking down on a top shoe shifting plate, and opposing pairs of top plate and bottom plate shoes, respectively.
Figure 7:
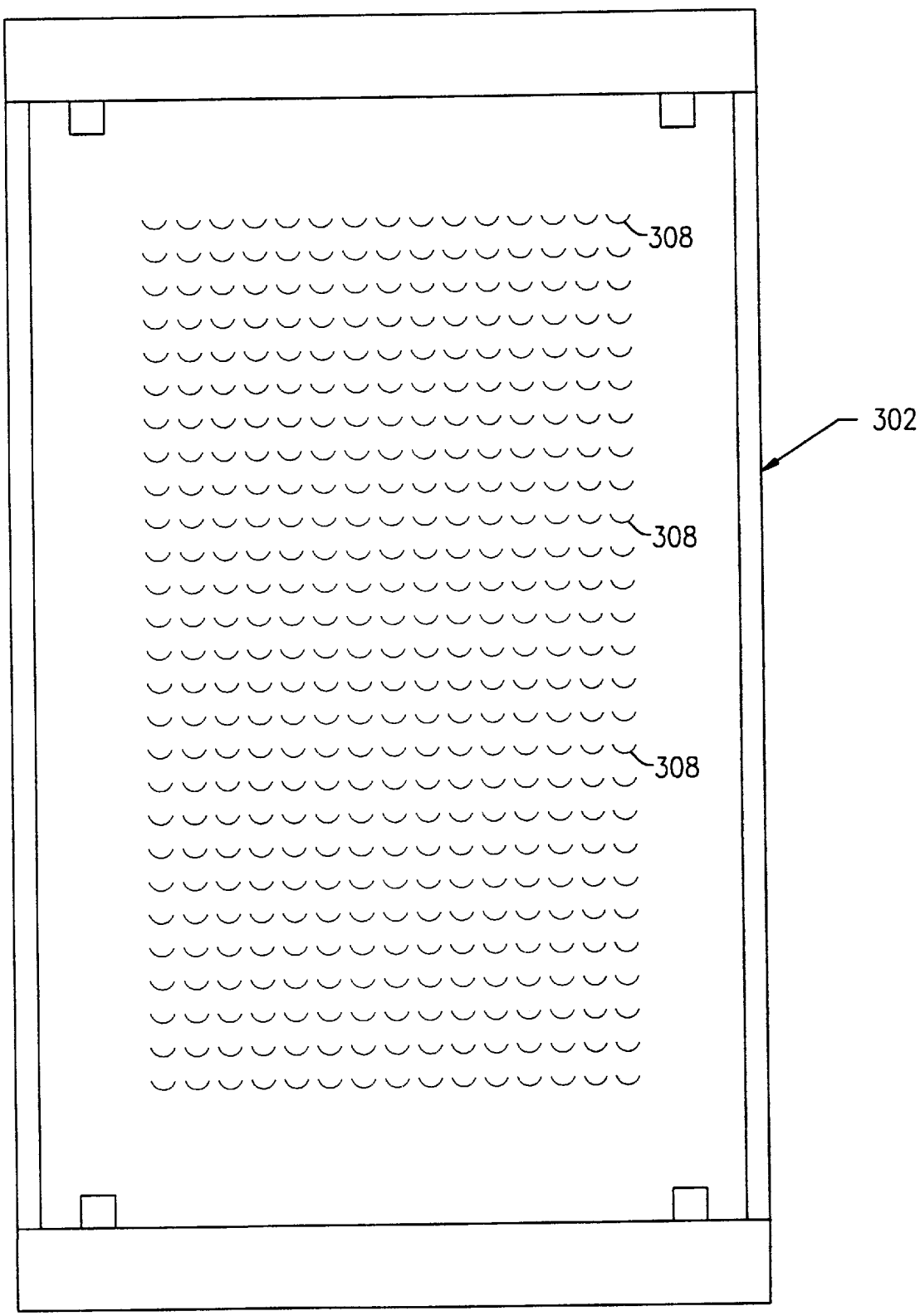
FIG. 7 is a top view of a bottom shoe shifting plate containing a plurality of bottom plate shoes designated as left-hand shoes.
Figure 8:
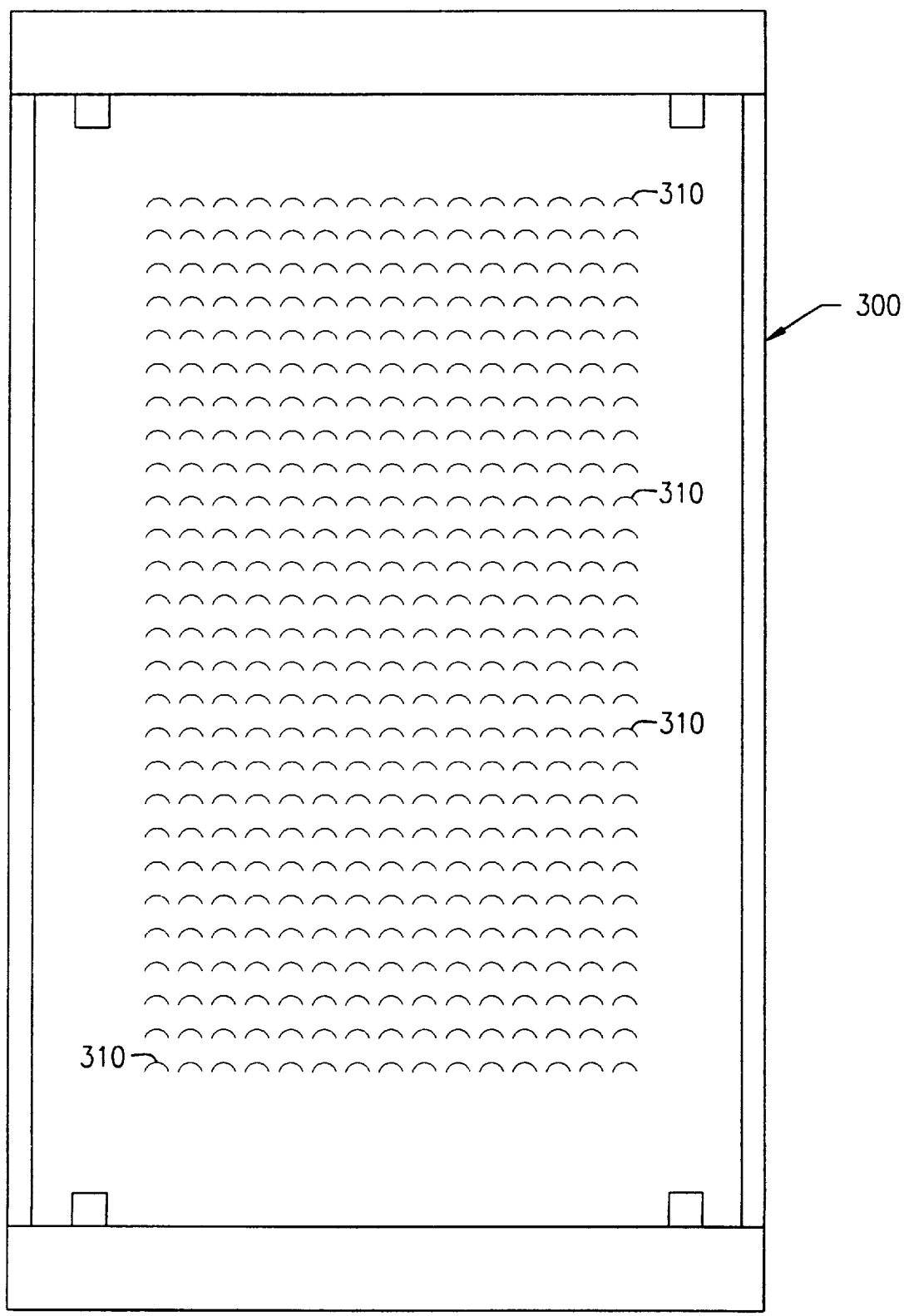
FIG. 8 is a top view of a top shoe shifting plate with a plurality of top plate shoes designated as right-hand shoes.

In FIG. 6, a top view looking downward upon the top shoe shifting plate 300, shows that in this example there are fifteen columns by twenty-seven rows of pairs of top plate or right-hand shoes 310 and bottom plate or left-hand shoes 308, the pairs totaling 405. Note that with respect to the right- and left-hand orientation, FIG. 6 is being viewed from the right side of the drawing looking in toward the right side of the top shoe shifting plate 300. The bottom plate shoes or left-hand shoes 308 of the bottom shoe shifting plate are shown in FIG. 7 looking down upon the top of the bottom shoe shifting plate 302. The bottom plate shoes 308 project through holes (not shown) in the top shoe shifting plate 300 to be positioned in opposing relationship with their respective top plate shoes 310, as shown in FIG. 6. In this regard, as shown in FIG. 8, the top plate or right-hand shoes 310 are positioned as shown on the top shoe shifting plate 300 prior to moving the bottom plate shoes 308 through holes in the top shoe shifting plate 300 (the holes are not shown in this example) for positioning in opposing relationship with respective ones of the top plate or right-hand shoes 310.

Figure 9:
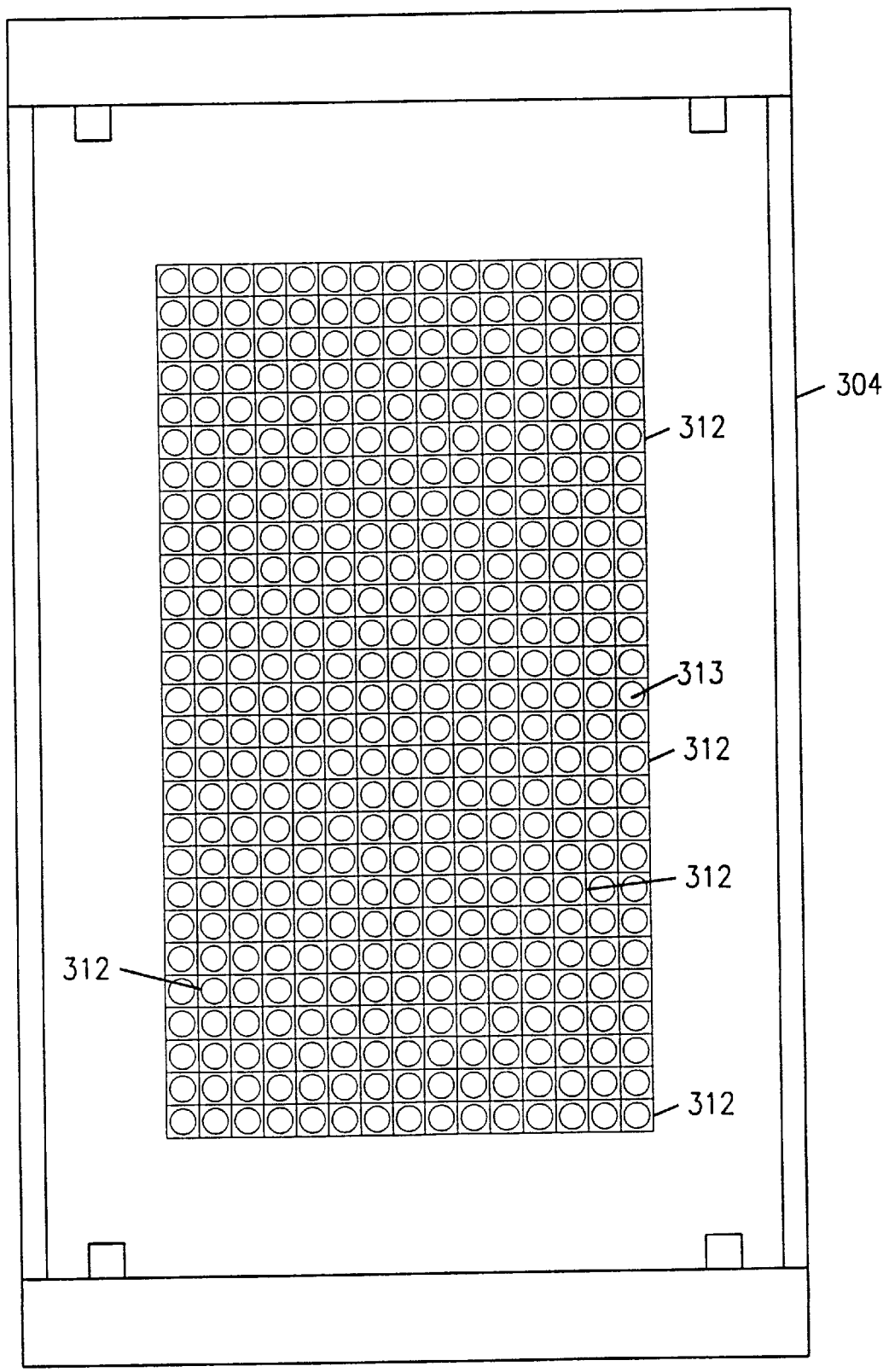
FIG. 9 is a top view of an insert table containing a plurality of takeoff inserts for the takeoff station of FIG. 5.

A top view of the insert table 304 is shown in FIG. 9. The takeoff inserts 312 are in this example positioned adjacent to one another and in juxtaposition, in a configuration of fifteen columns by twenty- seven rows, as shown. Each insert 312 includes a hole 313 that is circular in this example, and is concentric with and smaller in diameter than the diameters of both an underlying hole (not shown) through insert table 304, and a rolled up condom.

Figure 10:
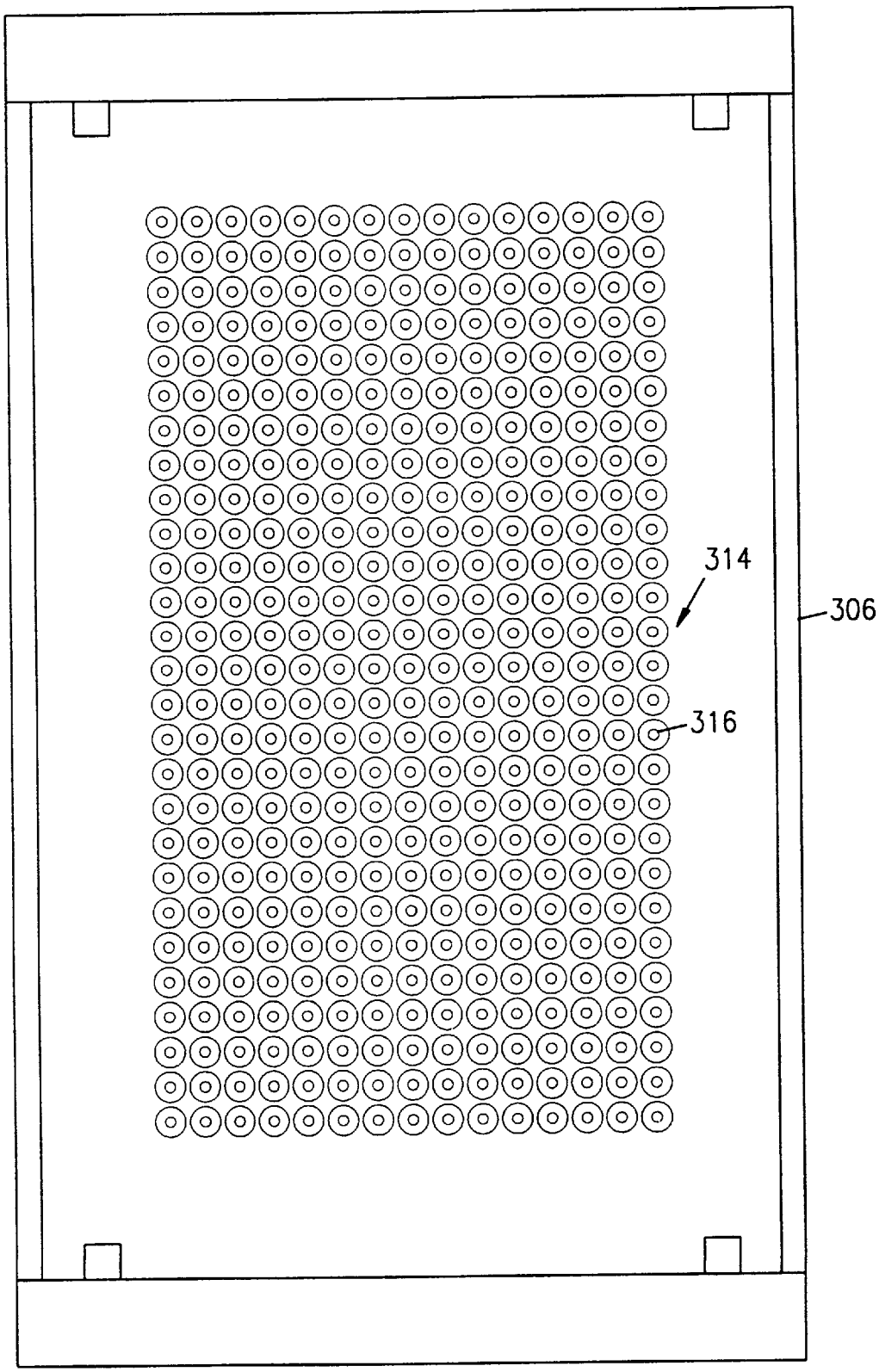
FIG. 10 is a top view of a air nipple table including an air nipple assembly containing a plurality of individual air nipples, for the takeoff station of FIG. 5.

FIG. 10 shows a top view of the air nipple assembly 314 looking down upon the air nipple table 306. As shown, the air nipple assembly 314 includes fifteen columns by twenty-seven rows of air nipples 316, which are juxtaposed to one another.

Note that in an engineering prototype machine, the right-hand and left-hand shoes 310, 308 were made from Amodel®, the takeoff inserts 312 from Delrin®, and the air nipples 316 from Teflon®. However, any other suitable materials can be used.

Figure 11:
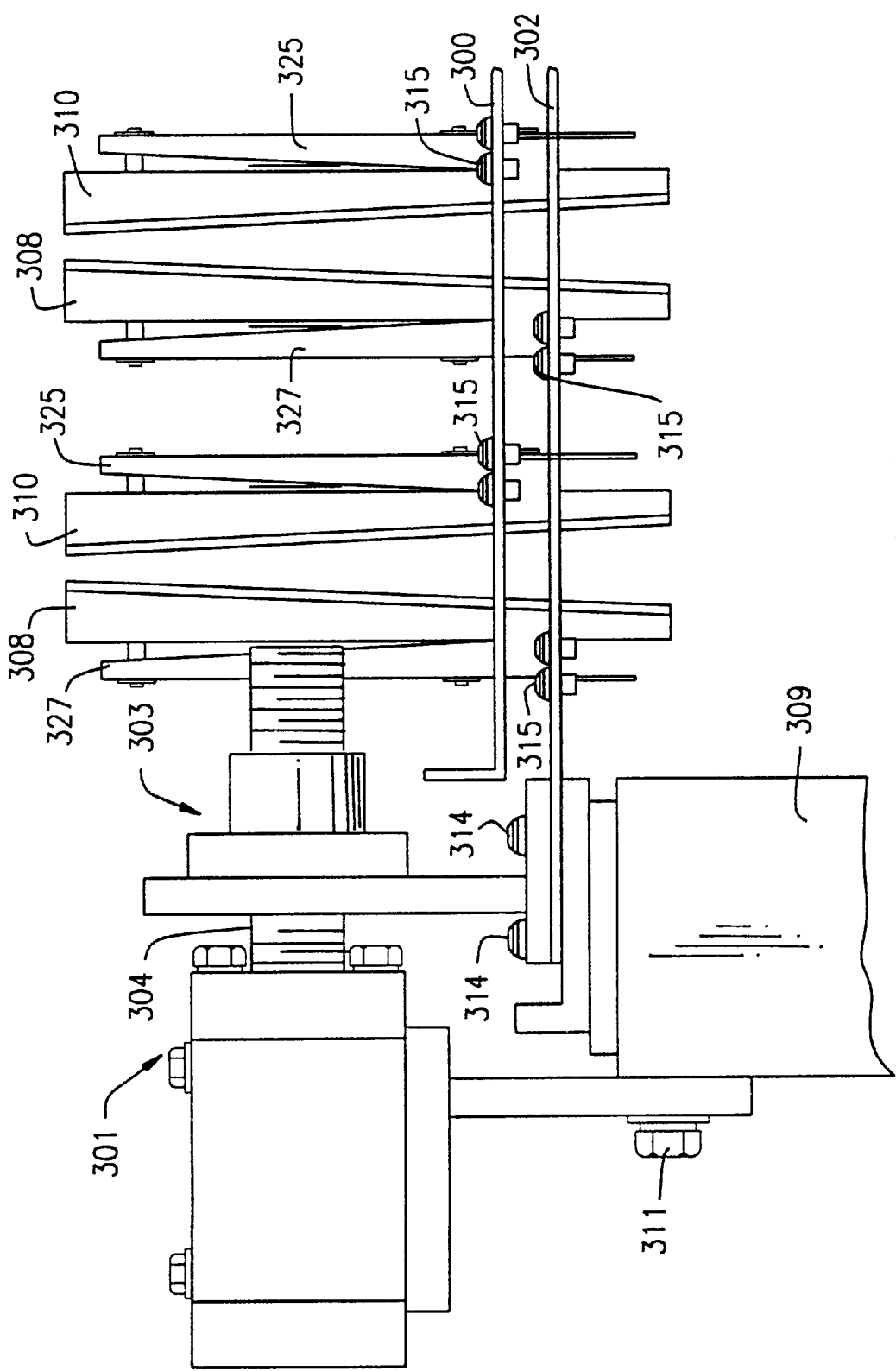
FIG. 11 is a side view of a portion of the assembly of the top and bottom shifting plates, and associated gear assemblies for moving the plates in a reciprocal manner to move pairs of the left-hand- and right-hand shoes either toward one another or away from one another.

In FIG. 11 a simplified view is shown of a portion of the mechanism for providing reciprocal motion between the top and bottom shoe shifting plates 300 and 302, respectively, whereby if one plate is moving in one direction, the other is moving in the opposite direction. In this manner, each of the pairs of shoes 308, 310 are selectively moved toward one another, or away from one another, as will be explained in greater detail below. A support post 309 has a gear box assembly 301 bolted to it via a bolts 311, as shown. Another gear assembly 303 is mounted upon the bottom shoe shifting plate 302 via the button head screws 314. The gear box 301 is driven by a stepper motor (not shown) for causing a screw 304 to rotate in a clockwise or counterclockwise direction for causing the gear assembly 303 to move back-and-forth on the screw 304, for in turn causing the bottom shoe shifting plate 302 to move in the direction of the gear assembly 303. A rack and pinion gearing located between the shifting plates 300 and 302, causes the top shoe shifting plate 300 to move in a direction opposite to that of the bottom shoe shifting plate 302. Note that the bottom plate shoes 308 are secured to bottom shoe brackets 327, which in turn are secured to the bottom shoe shifting plate 302. Similarly, the top plate shoes 310 are secured via shoe brackets 325 to the top shoe shifting plate 300.

Figure 12B:
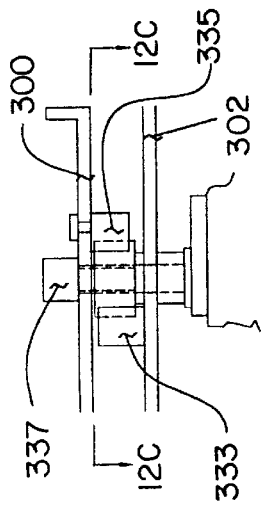
FIG. 12B is a side view of a portion of rack pinion gear mechanism for providing reciprocal and opposite movement between the top and bottom shoe shifting plates, respectively, for an embodiment of the invention.
Figure 12C:
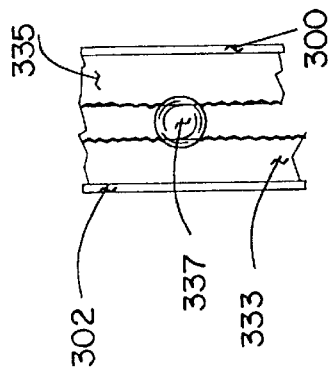
FIG. 12C shows a top view of a portion of the gear mechanism of FIG. 12B.
Figure 12A:
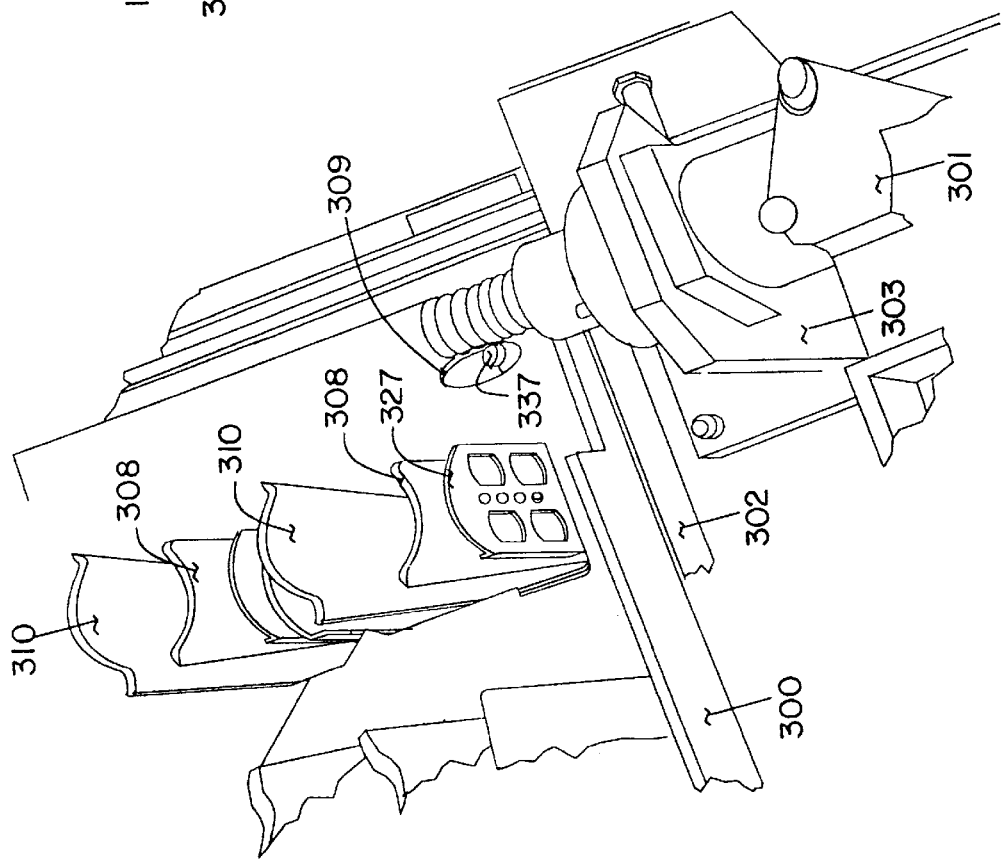
FIG. 12A is a partial pictorial view of the assembly of FIG. 11 viewed from a different direction.

In FIG. 12A, a partial pictorial view looking in at an angle is shown of the top shoe shifting plate 300, a number of bottom plate and top plate shoes 308, 310, and the gear box 301, and gear assembly 303. A portion of the rack and pinion gearing can be seen through an oval hole 309, in this example, in the top shoe shifting plate 300. Details of the rack and pinion gear mechanism between the top shoe shifting plate 300 and bottom shoe shifting plate 302 are shown as a side view in FIG. 12B, and as a top view in FIG. 12C. As shown, the rack and pinion gearing includes a rack gear 333 mounted on the bottom shoe shifting plate 302, and a pinion gear 337 connected between rack gear 333 and a rack gear 335 mounted on the bottom of the top shoe shifting plate 300.

Figure 13:
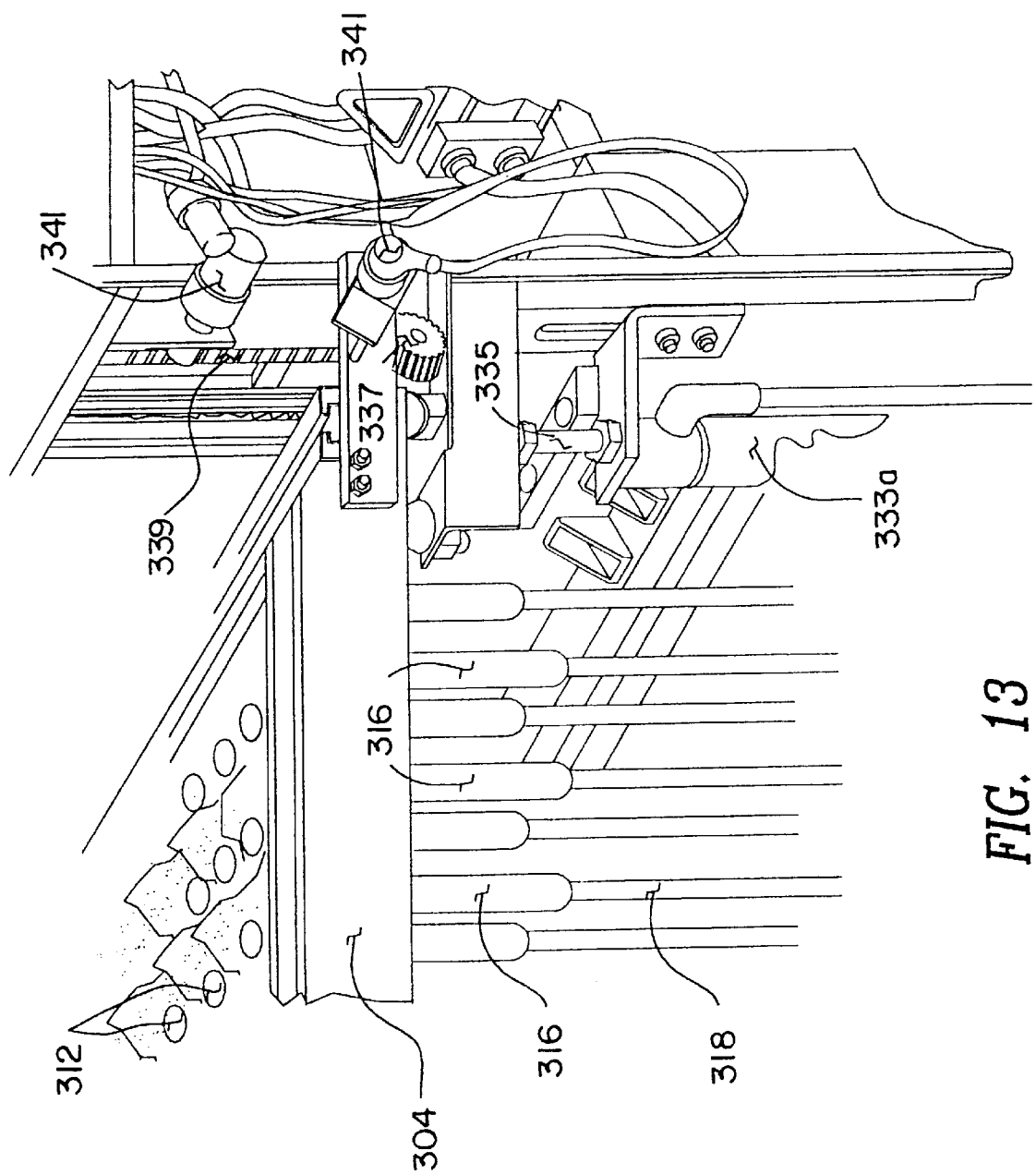
FIG. 13 is a partial pictorial view of a portion of the takeoff insert table in association with air assist cylinders and power driven gearing for raising and lowing the insert table, and further shows a portion of the associated air nipple assembly for the takeoff mechanism of FIG. 5.

In FIG. 13, a pictorial view is shown of a corner portion of the mechanism used for raising and lowing the insert table 304 remains level during lifting and lowering. A pinion gear 337 contacts with a rack gear 339 for providing a means to insure the insert table 304 remains level during lifting and lowering. Lifting and lowering power is provided by a pneumatic cylinder 333a for providing power to lift and lower the insert table 304. Note that four air cylinders areh used, with one being located in each corner of the insert table 304 (e.g. see cylinder 333b in FIG. 21). A plurality of position detecting transducers are used in the system, two of which (341 and 343) are shown in FIG. 13. Such detectors may act as a means for limiting the upward or downward movement particular ones of the mechanical assemblies of the takeoff station 90 mechanism, and as housing means.

Figure 14:
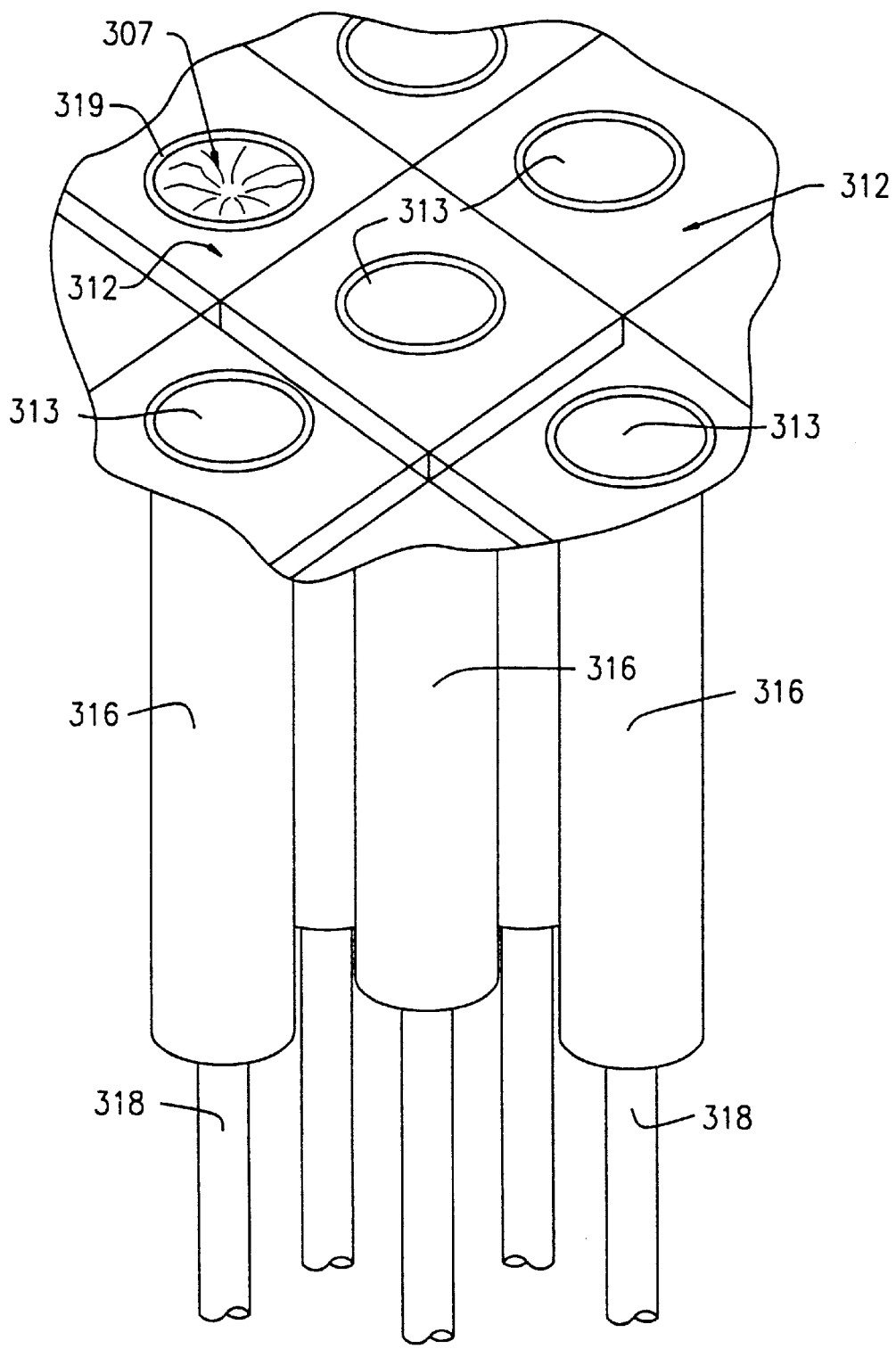
FIG. 14 is an enlarged pictorial view of a portion of an array of takeoff inserts relative to associated air nipples for the takeoff mechanism of FIG. 5.

In FIG. 14, an enlarged view of a number of air nipples 316 located beneath a plurality of takeoff inserts 312 is shown. Each of the takeoff inserts 312 includes a circular hole 313 that has a chamfer about the circumference of the underlying holes of insert table 304. As will be explained below, a condom 307 removed from a mandrel 176, will during one phase of the takeoff operation be held on top of its associated takeoff insert 312, as shown on one of the inserts 312 in FIG. 14 in the upper left-hand portion. Note that the overall takeoff geometry described herein can be changed to accommodate different products.

Figure 15:
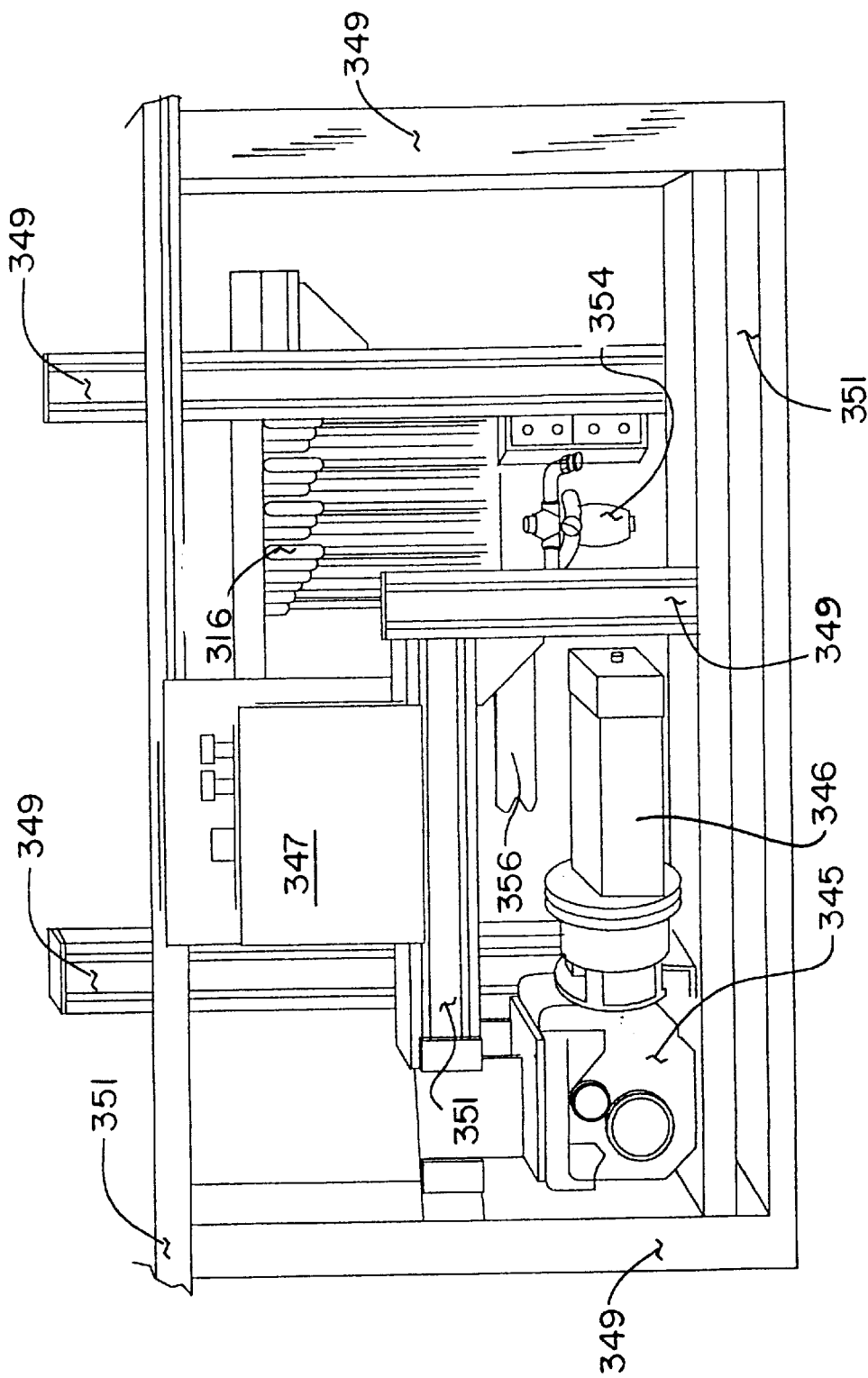
FIG. 15 is a partial pictorial view of various gearing, motor, and air valve mechanism associated with the takeoff mechanism of FIG. 5.

FIG. 15 is a pictorial view of a portion of the takeoff apparatus including a gear box 345 that is driven by a servo motor assembly 346 for moving the air nipple table 306 (see FIG. 5). Also shown in FIG. 15 are vertical frame members 349, lateral frame members 351, an air regulator 354 supplying an air manifold 356 for connection to the air nipple table 306, and electrical box 347. Note the relative locations of the insert table 304, and air nipples 316, as partially shown in FIG. 15.

Figure 16:
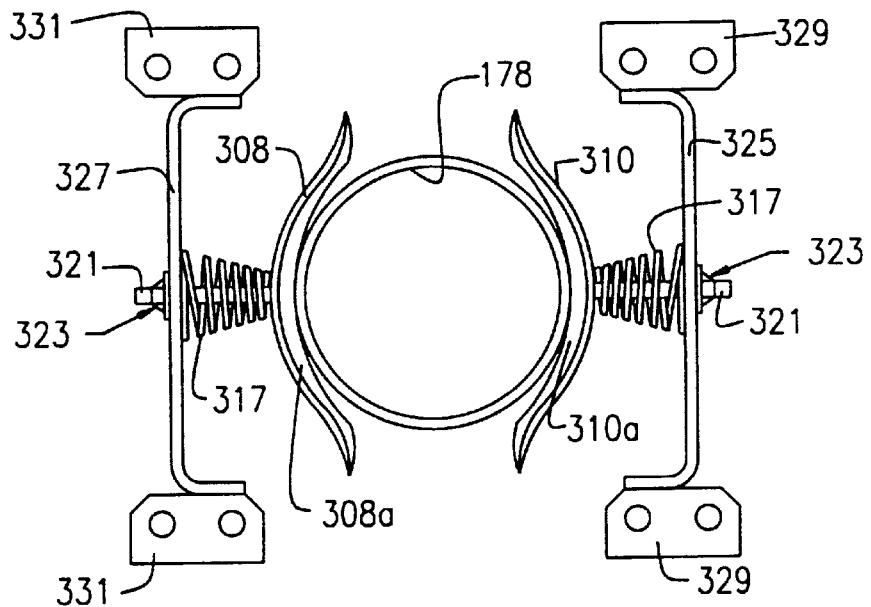
FIG. 16 shows a top view of a shoe assembly in a closed position relative to an associated mandrel.

As shown in FIG. 16, looking down at a mandrel 178 located between a bottom plate shoe 308 and a top plate shoe 310, the shoes are resiliently mounted to their respective shoe brackets 327, 325. More specifically, a bottom plate shoe 308 is mounted via two mounting posts 321 to a bottom plate shoe bracket 327. A helical spring 317 is mounted on a post 321 of shoe 308 between shoe 308 and the inside face of the shoe bracket 327. The mounting post 321 is secured to the outside face of the shoe bracket 327 via a retainer clip 323, as shown. Similarly, the opposing top plate shoe 310 is resiliently mounted to its associated top shoe bracket 325. Note that the bottom shoe brackets 327 are secured to the bottom shoe shifting plate 302 via mounting feet 331 located at the bottom of the brackets 327, and similarly the top shoe brackets 325 are mounted on the top shoe shifting plate 300 via mounting feet 329 located at the bottom of the shoe brackets 325. The spring biasing provided by the helical springs 317 is used to substantially reduce the chance of damaging a condom 307 on a glass mandrel 178 due to excess force being applied by the pairs of shoes 308 and 310 when they move toward one another and close upon their associated mandrels 178, as will be explained in greater detail below.

Figure 17:
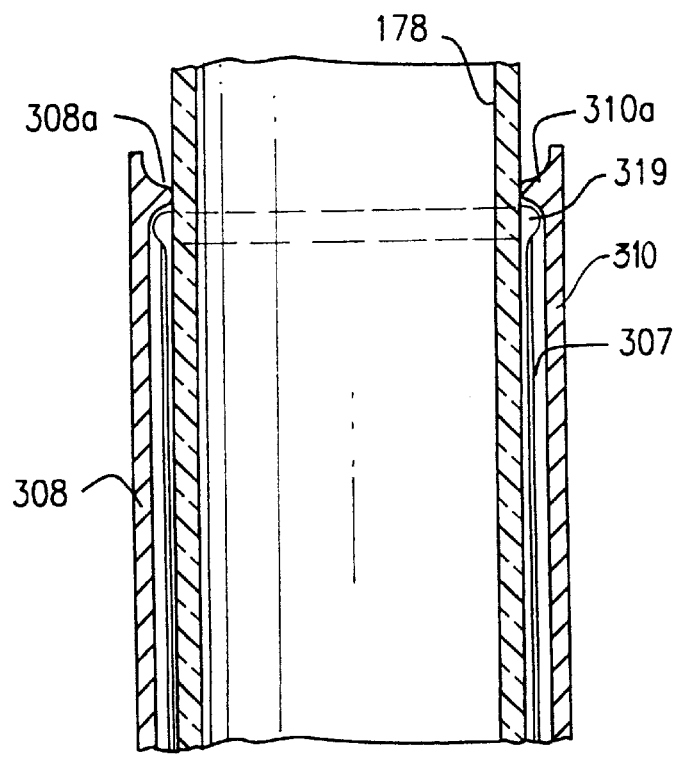
FIG. 17 is a detailed partial cross-sectional view of a mandrel carrying a condom with a pair of opposing shoes in a closed position just after partially rolling a condom for removing the condom from the mandrel.
Figure 18:
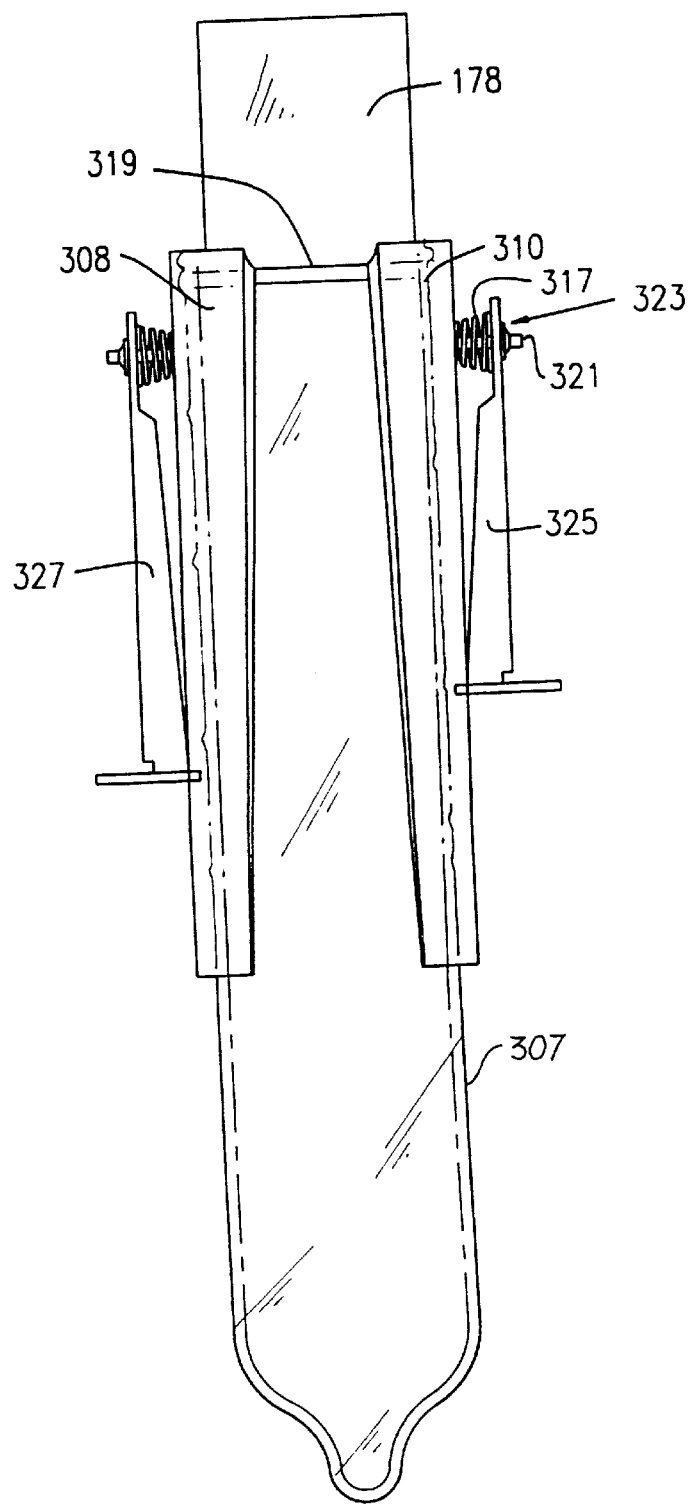
FIG. 18 is a partial pictorial view showing a substantial portion of a mandrel 178 carrying a condom, with the associated shoe assembly in a closed position as in FIG. 17 for removal of the condom.
Figure 19:
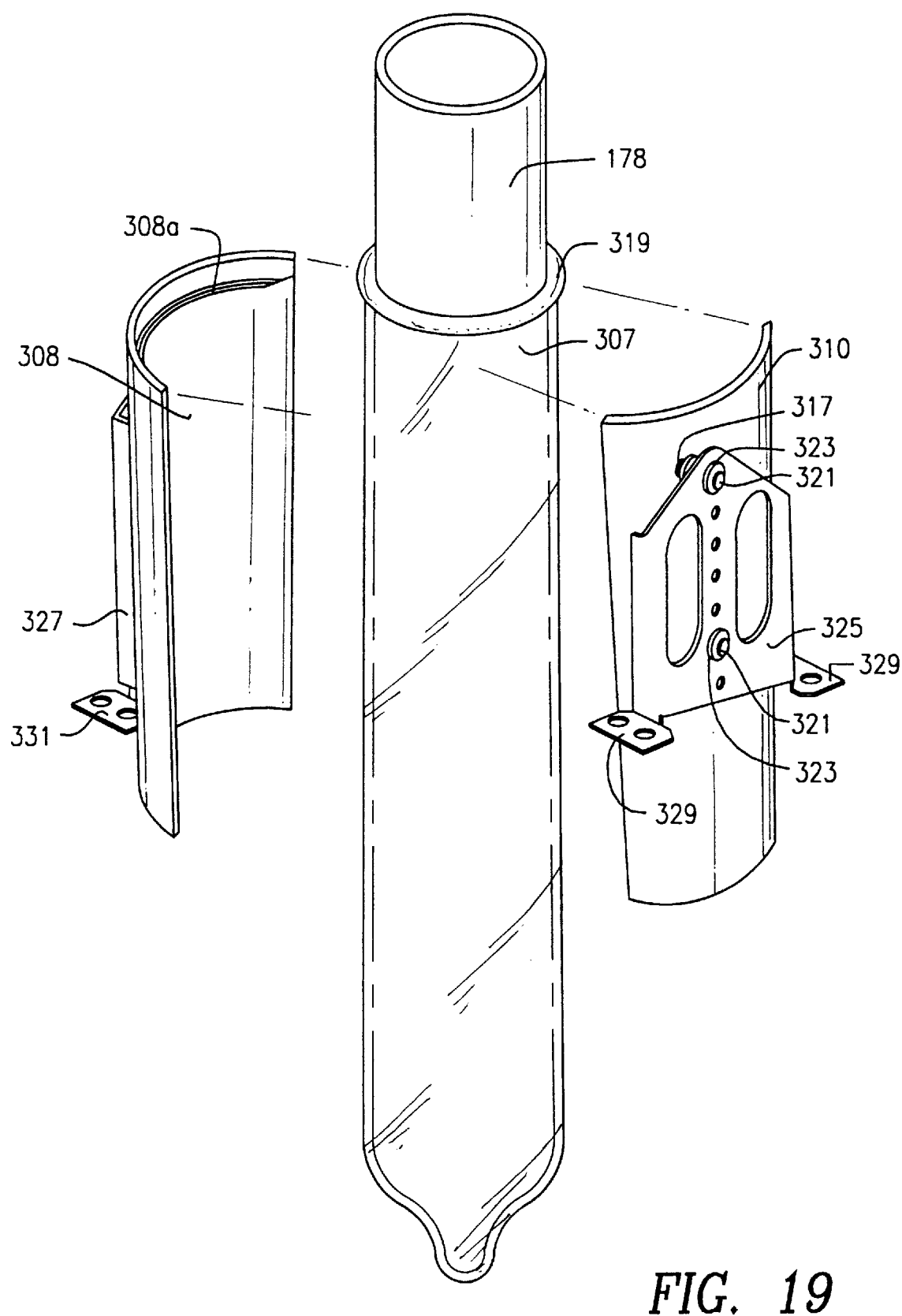
FIG. 19 is a pictorial view showing a mandrel carrying a condom with the associated shoes in an open position, with the open position being exaggerated for purposes of illustration.

With reference to both FIGS. 16 and 17, note that each one of the shoes 308 and 310 include a projecting flange 308a, and 310a, respectively. Also, the cross-sectional view of FIG. 17 shows the shoes 308 and 310 in a closed position upon a mandrel 178 just after partially rolling up the condom 307 to remove it from the mandrel 178. Note that the closed pair of shoes 308 and 310 provide for engaging a respective condom 307, whereby as will be explained in greater detail below, when mandrel 178 is moved upward to a position shown in FIG. 17, this movement causes the condom 307 to be rolled downward toward the end of the mandrel 178. In FIG. 18, a more complete pictorial view is provided for showing substantially the entire mandrel 178 carrying a condom 307 formed thereon, along with two mounting brackets 325 and 327, and the associated other mechanical features described for FIG. 16 above. In FIG. 19, the pair of shoes 308 and 310 are shown in an open position before being moved into engagement with the condom 307 after mandrel 178 is raised a predetermined amount, as previously described.

Figure 20:
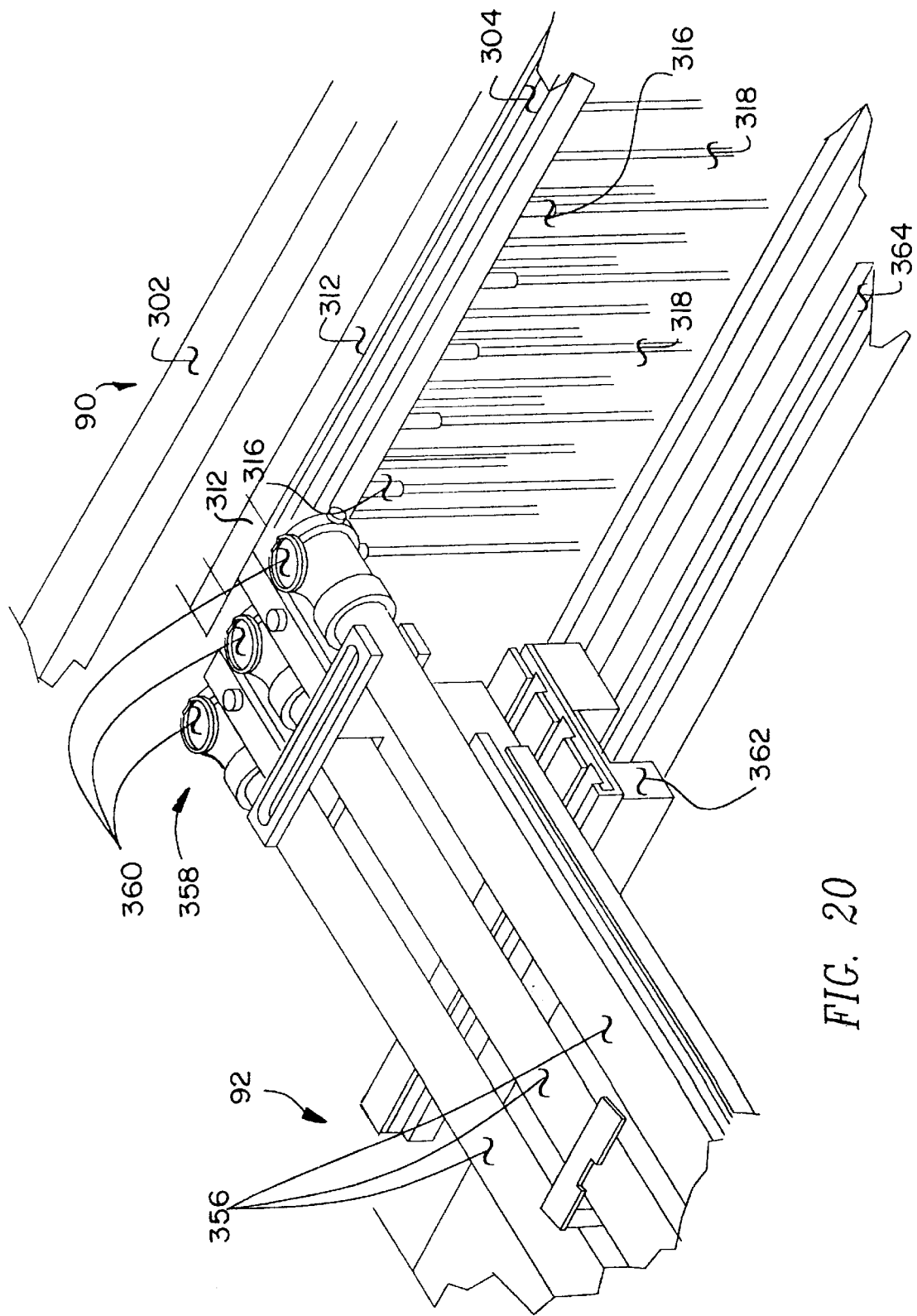
FIG. 20 is a partial pictorial view of a "snapper assembly" in relation to portions of the takeoff mechanism of FIG. 5, whereby the X-Y snapper assembly is moveable relative to the takeoff mechanism.
Figure 21:
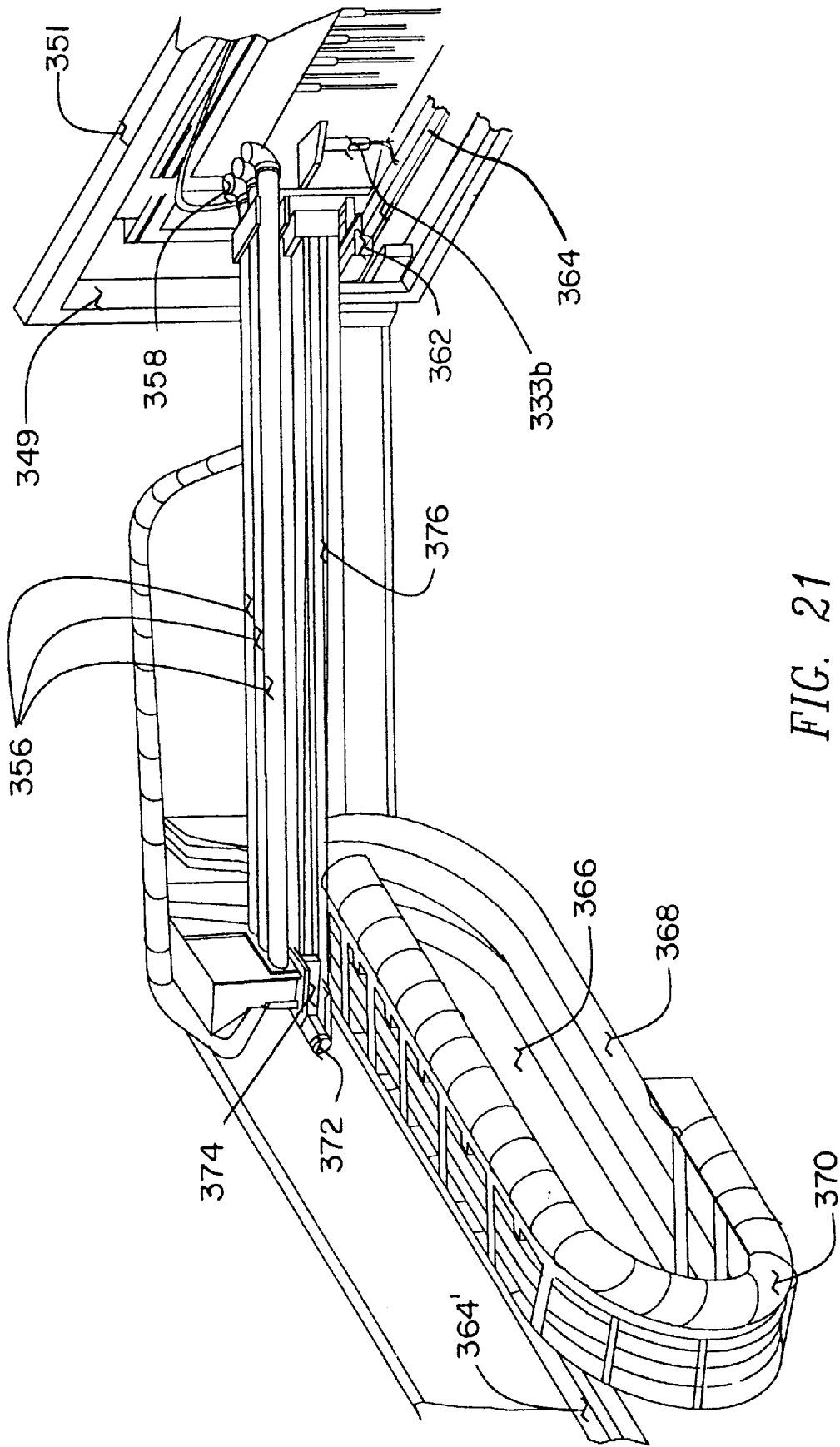
FIG. 21 is a partial pictorial view showing additional portions of the X-Y snapper mechanism of FIG. 20 in conjunction with a portion of the takeoff mechanism of FIG. 5.

After the condoms 307 have been removed from their respective mandrels 178, and powdered at the interior of their closed ends, the condoms 307 are resting on top of the takeoff inserts 312, respectively, awaiting removal from the takeoff station 90, as will be explained in greater detail below. The condoms 307 are removed from the takeoff insert 312 via the X-Y snapper station 92 (see FIG. 1A), a portion of which is shown in FIG. 20. As shown, a plurality of snapper tubes 356, three in this example, each have a snapper suction nozzle 358 attached to their open end proximate takeoff station 90 (see FIG. 1A). A portion of the snapper tubes 356 are mounted upon a trolley 362 for moving the nozzles 358 transverse to the insert table 304, that is in the X-direction, in this example. A track 364 is provided for the trolley 362. The nozzles 358 each have a condom entry 360, as shown, and as further shown in FIG. 21, the X-Y snapper station 92 also includes suction tube CAT racks 366 including links 370 for carrying flexible suction tubes 368, as shown. The flexible suction tubes 368 are connected to the ends of the suction tubes 356 opposite the suction nozzles 358, as shown. A motor 372 is located for driving a trolley 374 for moving the suction tubes 356 and associated nozzles 358 into position under the insert table 304 for sucking up condoms 307 from the takeoff inserts 312. In this regard, note that trolley 374 is driven for moving the suction nozzles 358 in a Y-direction under the insert table 304, whereas trolley 362 is motor driven (motor not shown) for moving the nozzles 358 in an X-direction, as previously mentioned. Note also a track 364' is located for permitting another X-movement trolley (not shown) to move transversely in the same manner as trolley 362.

An enlarged and detailed view of the assembly of the nozzle 358 is shown in FIG. 22A, and in FIG. 22B. With reference first to FIG. 22A, the snapper tubes 356 are secured into position at the nozzle end between a top plate 378 and bottom plate 382, between which spacers 384 are located as shown. The plates 378, 382 are secured to the spacers 384 through use of screws 379, as shown. Bushings 380 are located as shown on the projecting fingers 381 of the top plate 378. The hard bushings 380 are made higher than the top of the nozzles 358 to adjust the spacing of the nozzles 358 from the bottom surface of the insert table 304. The bushings 380 are typically made of Nylatron®, or UHMW®, or other suitable plastic material. The bottom front portion 390 of each of the nozzles 358, include an opening 392 (see FIG. 22B), in which is mounted a butterfly valve 388 that is rotatable about an axle 387 secured at each end of the collar like member 390 via a retainer cap 386. The butterfly valve 388 is rotated to close off the opening 392 of its associated nozzle 358 when the nozzle 358 is positioned for sucking a condom from a takeoff insert 312. At other times, the butterfly valve 388 is positioned to open the port hole 392. The port 392 is kept open at all times other than when a condom 307 is to be removed from a takeoff insert 312, to avoid excess vacuum pressure that may pull condoms off of the takeoff inserts 312 at an undesirable angle, causing damage to the condoms 307.

In FIG. 24 a top view is shown of an air nipple 316, and in FIG. 23 a partial cross-sectional and pictorial view is shown of the air nipple 316 as installed in a air nipple assembly 314. As shown, an air connector assembly 320 is secured to the top of the air nipple table 306 (see FIG. 5). The bottom of the associated tubing 318 is secured to the air connector assembly 320 by air seal collar 404. Air nipple 316 is held captive on the other end of the tubing 318 via a roll pin 394, as shown. The air nipple 316 includes a slot way 396 to permit the air nipple 316 to move vertically in a range by sliding on the tube 318, with the roll pin 394 also providing a stop for limiting downward movement. A spring 398 is positioned as shown between the top of tubing 318 and the top of a hole 399 extending through the air nipple 316 from the bottom to a point just below the nipple-like top portion or tip 397. A recess 400 is provided in the top of the air nipple 316 for receiving a Gore-tex® insert, in this example, to cushion any contact between the tops of the air nipples 316 and the bottoms of the condoms 307 on glass mandrels 178 during manufacture of the condoms 307. As further shown in the top view of the air nipple 316 in FIG. 24, four orifices 406 are included about the circumference of the top portion 397. In this manner, air driven through air inlet 402 and exiting from the orifices holes 406, causes a condom 307 resting upon the nipple portion 397 to remain inflated during the application of powder to the exposed areas of the condom 307, and also causes the condom's tip to be inverted.

Figure 25B:
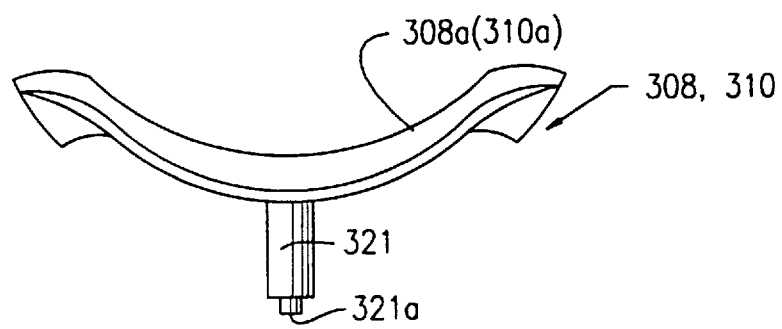
FIG. 25B is a top view of the shoe of FIG. 25A.
Figure 25A:
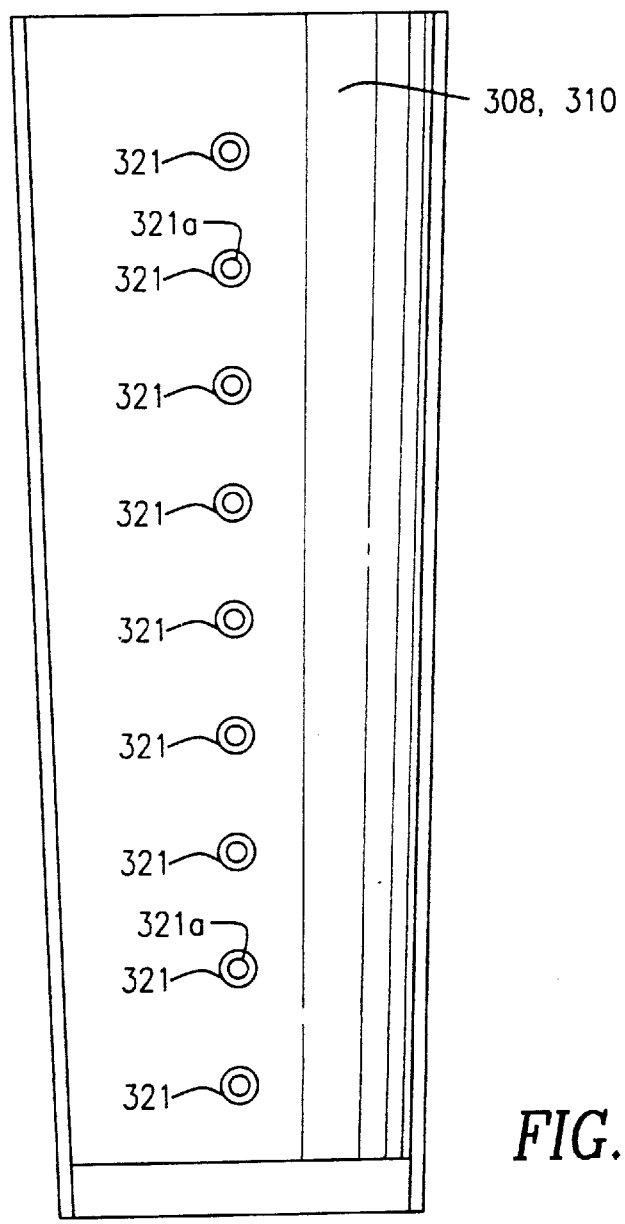
FIG. 25A is a backside view of a shoe assembly for the takeoff mechanism of FIG. 5.
Figures 26A, 26B:
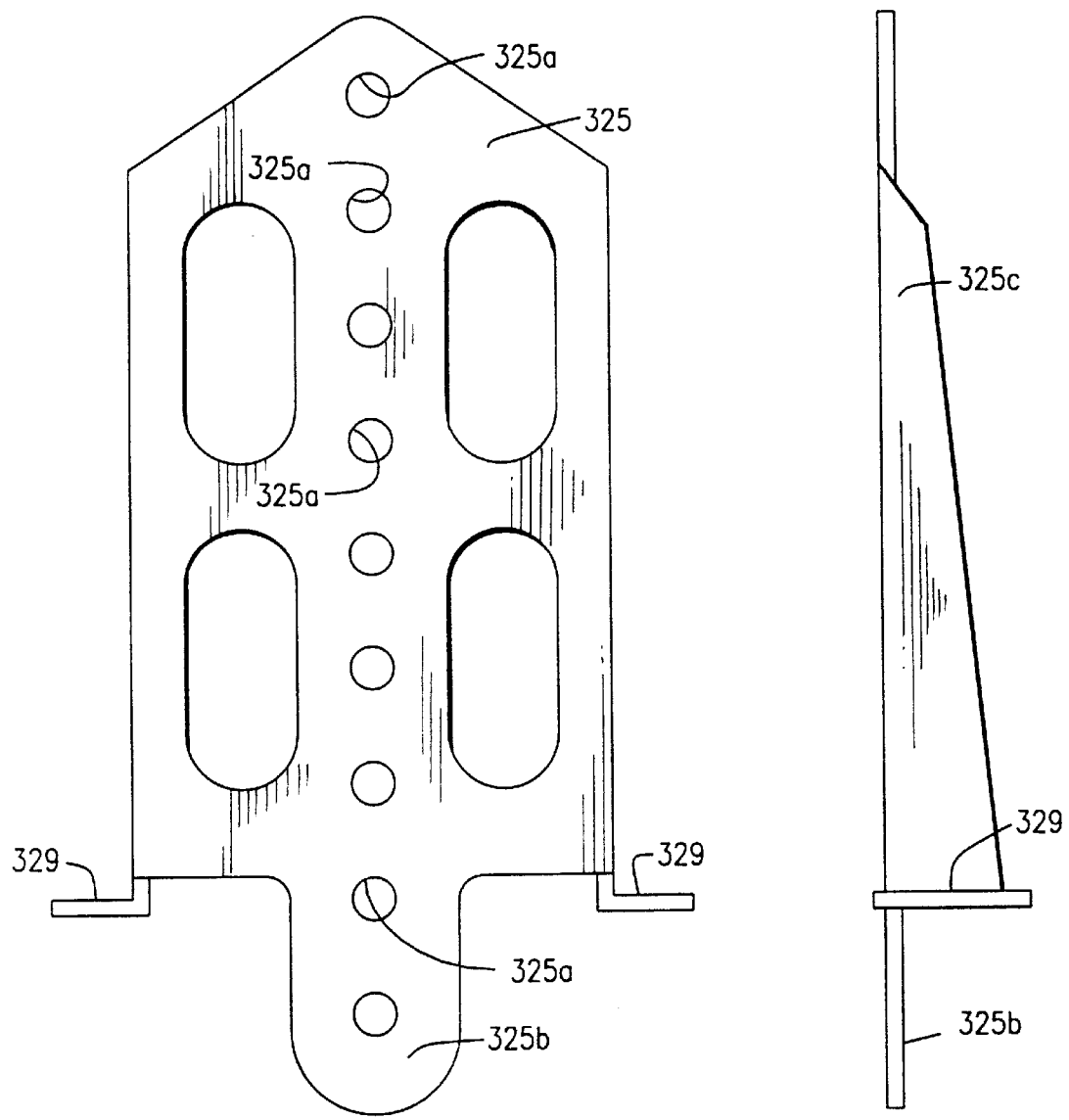
FIG. 26A shows a back view of a shoe bracket for a top plate shoe or right-hand shoe.
FIG. 26B shows a side view of the shoe bracket of FIG. 26A.
Figures 27A, 27B:
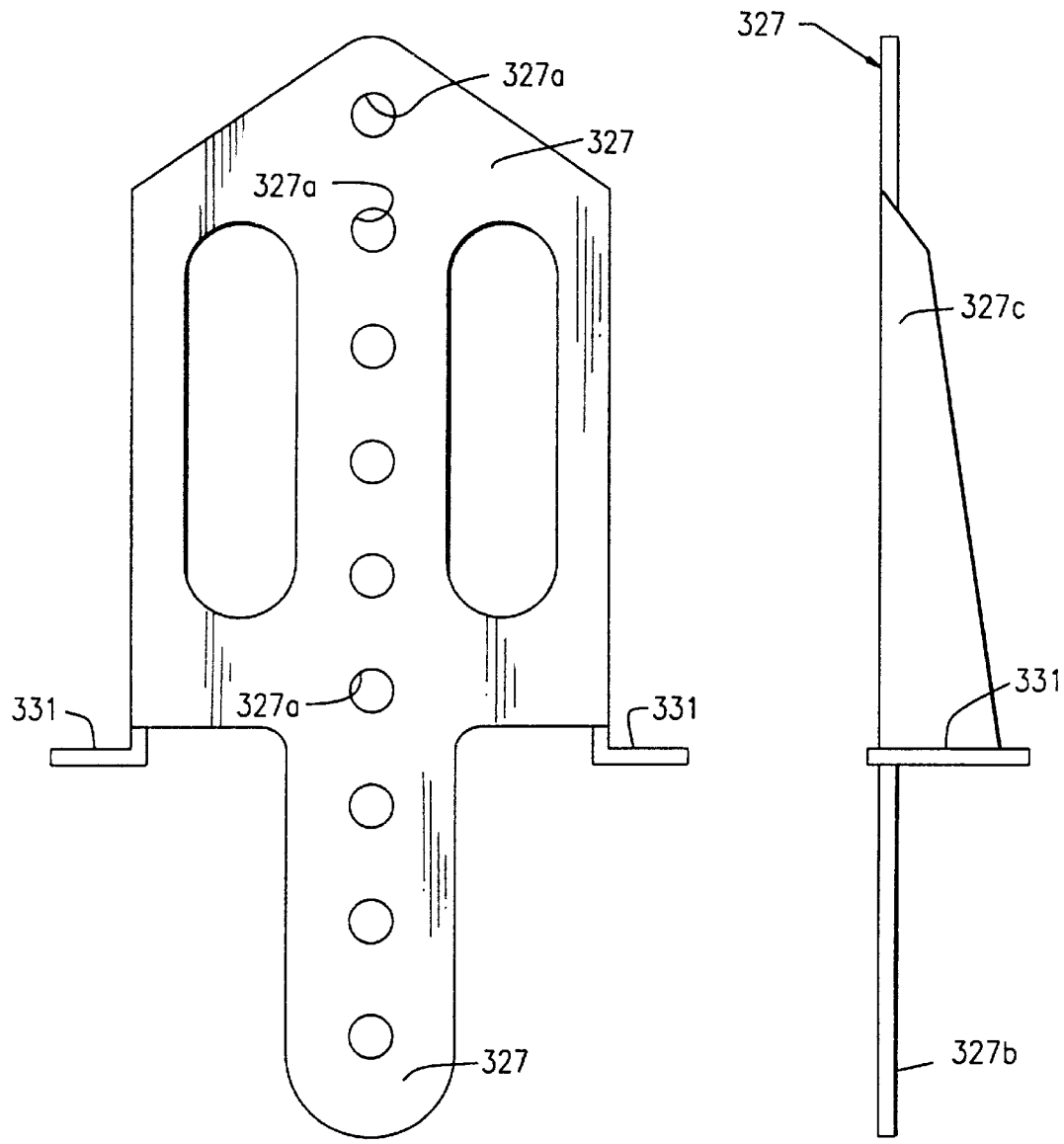
FIG. 27A shows a back view of a shoe bracket for a bottom plate shoe or left-hand shoe.
FIG. 27B shows a side view of the shoe bracket of FIG. 27A.

Greater details of the configuration of the shoes 308 and 310 are provided in FIG. 25A showing a back view of the shoes 308, 310, and a top view thereof as shown in FIG. 25B. Note that a plurality of mounting posts 321 are vertically orientated, spaced apart, and located in the center in the back of each of the shoes 308, 310, as shown. Note that the mounting posts 321 each include a reduced diameter tip 321a for receiving a retainer clip 323, as previously explained. Greater details of a top shoe mounting bracket 325 are shown in FIG. 26A. Note that a plurality of holes 325a are provided for receiving the tips 321a of the mounting post 321. The mounting flanges 329 are used to secure the shoe bracket 325 to the top of the top shoe shifting plate 300. As shown in FIG. 26B, the shoe bracket 325 includes a lower extended portion 325b from opposing side flanges 325c. Similarly, as shown in FIG. 27A, and FIG. 27B, the bottom shoe mounting brackets 327 includes a plurality of holes 327a for receiving the reduced diameter tips 321a of a shoe 308, and mounting feet or flanges 331. Also, opposing side flanges 327c are provided as shown in FIG. 27B. Note that the bottom extended portion 327b of the bottom shoe bracket 327 is longer than the extended portion 325b of the top shoe bracket 325, for permitting the bottom plate shoes 308 to be properly positioned relatively to the top plate shoes 310, in this example. Note also that many other configurations can be used for providing the mounting of the shoes 308 and 310, and the present configuration as shown is not meant to be limiting. Nor are any other features as described above meant to be limiting.

With reference particularly to FIGS. 1A, 5, 6, 9, 10, 12A–C, 13, 14, 17, and 19 through 24, the operation for the take off mechanism begins with the dipping transport unit 85 which includes the carrier or pallet 176 for the mandrels 178 positioned with the polyurethane condoms 307 formed on mandrels 178 ready for takeoff over the takeoff station 90. Note that each of the pairs of shoes 308, 310, are opened by moving the top and bottom shoe plates 300, 302, respectively, in opposite directions to move the individual shoes 308 away from their associated shoes 310, respectively. To close each pair of shoes 308, 310, the movement of the shoe plates 300, 302, is reversed. The take off operation is initiated by opening the pairs of shoes 308, 310 on the take off mechanism, followed by lowering the pallet 176 to lower the mandrels 178. Once the respective pairs of shoes are opened, the mandrels 178 are lowered for the first stroke and the ring 319 of each condom is positioned near the bottom of the associated shoes 308, 310. The respective shoes 308, 310 are then closed to a predetermined position, and then the pallet 176 is moved upward rolling the condoms 307 approximately one-third down their associated glass mandrels 178 (see FIGS. 17 and 18) via the frictional contact between shoes 308 and 310 and the rings 319 of the condoms 307 (see FIG. 19). The shoes 308, 310 are opened again, and the condoms 307 and associated mandrels 178 are repositioned with the rings 319 at the bottom of their associated shoes 308, 310. The individual pairs of shoes 308, 310 are then closed to a predetermined position against the ring 319 of their associated condom 307, and again the associated mandrels 178 are withdrawn or moved upward for rolling the associated condoms 307 approximately three-quarters or more down their respective mandrel 178. In the final and third stroke, the pairs of shoes 308, 310 are opened again, the associated mandrels 178 are reinserted their required depth into their associated pairs of shoes 308, 310, respectively, and the shoes 308, 310 are closed. At this time, the air nipple table 306 holding the four-hundred-and-five air nipples 316, in this example, is raised with air blowing out of orifices 406 of nipples 316, respectively, and then transfers upward at the same rate of upward movement of the glass associated mandrels 178, respectively, maintaining about a sixteenth to a thirty-second inch space between the tip 397 of each air nipple 316, and the tip of the associated glass mandrel 178, while the associated condom 307 is being rolled up by its shoes 308, 310. At the final withdrawal, the tips 397 of each air nipple 316 are at a position above the shoes 308, 310 with the associated condoms 307 deposited on them in an inside out or upside down orientation mode, respectively. Next, the pairs of shoes 308 and 310 are opened. The air nipple table 306 is then lowered, causing the rolled up condoms 307 on respective air nipples 316 to move down through associated shoes, 308, 310. The condoms 307 are deposited on respective takeoff inserts 312 since the diameter of the condoms 307 is larger than the diameter of holes in the inserts 312. The associated air nipples 316 continue to move downward to a position below the insert table 304. Next, a set of tubes (not shown) underneath the bottom shoe shifting plate 302 sprays powder on the tips or nipples of the condoms 307, because at that time the tip is the only portion of each condom 307 that is unrolled and unpowdered. The powdering prevents condoms 307 from sticking together, and occurs just before the insert table 307 is raised up. After powdering, the insert table 304 is raised to an uppermost position, the X-Y snapper nozzles 358 are then swept underneath the insert table 304, for withdrawing or sucking the condoms 307 through the takeoff inserts 312 down through the snapper tubes 356, which at least partially unrolls the condoms 307. Note that both the chamfer and diameter of the hole through each of the takeoff inserts 312 are configured to maximize the extent of partially unrolling condoms 307 passing through, while preventing damage thereto. The takeoff inserts 312 can consist of any suitable material, such as a plastic material (Teflon®, nylon, and so forth).

The air nipple table 306 carrying the air nipple assemblies 314 (see FIG. 5), is raised and lowered by a servo motor (not shown) located to the side of the table 306 that is driving chain driven gears (not shown), along with an air assist lift mechanism (not shown) in order to take the load off the servo motor. The table 306 carrying the takeoff inserts 312 is driven upward and downward through use of a rack pinion mechanism 337, 339 connected to an air assist cylinder 333a (four cylinders are used, via at each corner, such as cylinder 333b in FIG. 21, but the two other air cylinders are not shown). The pairs of takeoff shoes 308, 310 are in opposing relationship, and are alternately connected to upper and lower or top and bottom shoe shifting plates 300, 302, respectively, as previously mentioned. The plates 300, 302 are driven in reciprocal motion through use of a rack pinion drive mechanism 333, 335, 337 that is driven by a single stepper motor (not shown). The stepper motor drives two-Gear Boxes (not shown) to drive rack pinion mechanisms (not shown) at either side of the plates 300, 302 upon which the shoes 308, 310 are mounted. Rotating rods (not shown) drive gears (not shown) that in turn drive a pinion gear 337 either clockwise or counterclockwise for causing the lower shoe plate 302 to move horizontally in one direction and the upper shoe plate 300 to move horizontally in the opposite direction, for simultaneously opening and closing all of the pairs of shoes 308, 310 of the takeoff station 90, in order to roll-up a condom 307 on each of the respective mandrels 178. The number of times that the shoes 308, 310 are so closed and opened, along with upward and lower movement of each one of the mandrels 178 is in this example as previously described in the above paragraphs. However, in other embodiments, the number of times of opening and closing shoes 308 and 310 can be more or less than three. The opposing shoes 308, 310 are retained on lower and upper plates 300, 302, respectively, via spring biasing attachment means, for permitting the shoes to resiliently contact the condoms during a takeoff cycle, as described in detail above.

A redress and inspection station 99 is located at the end of the drying section after the staging conveyor station 97, and permits the pallets 176 to be selectively brought out after washing and rinsing for access by the operators in order to either replace or tighten mandrels 178, strip-off any condom 307 that may have not been removed during prior processing, or otherwise make whatever repairs or adjustments that are necessary as previously mentioned. The nipple support Teflon® air nipples 316 each have a Goretex® tip in order to prevent cutting of a condom 307 if the tip of an associated condom 307 happens to come in contact with the bottom of one of the mandrel tubes 178. Also, the air nipple table 306 retains the air nipple assemblies 314. The air nipples 316 each have nipple holders formed at their tips 397 (see FIG. 23), and each have a manifold built into their bottom portions for permitting air to flow up through the center of the main support tubes 318, through the associated air nipples or tip 316, and out of small holes or orifices 406 in the center portion of the tip 397 of the air nipples 316, respectively, in order to expand the nipple portions of the condoms 307 for proper powdering. On the third stroke or step of the condom removal operation, the air nipples 316 move upward to lift up the condoms 307, then the shoes 308, 310 opened, and the air nipples 316 drop backdown, whereby the condoms 307 are deposited on the takeoff inserts 312 of the insert table 304, the insert table 304 moves down, followed by spray bars (not shown) being operated for spraying powder onto the nipple ends of the condoms 307, as previously described. Then the insert table 304 is raised, whereafter the X-Y snapper system 92 is operated in order to sweep the snapper suction heads 358 under the insert table 304 for sucking the condoms into the takeoff tubes 356, and then into a central tube (not shown) for deposit into a receptacle on the outside of the machine, as described in detail above.

Note that the datums or home positions are all established relative to a stepper motor (not shown) associated with the X-Y snapper system 92, and the stepper motor (not shown) associated with the shoe shifting plates 300, 302. A proximity detector or transducer is used in order to provide a datum signal for signaling the system that the shoe plates 308, 310 are at a home position. Note also that proximity sensors (not shown) are used for detecting whether the insert table 304, and the air nipple table 306 are in upper or lower positions, respectively. Note further that the air nipple table 304 uses a servomotor (not shown), whereas the X-Y snapper system 92 and the shoe plates 300, 302 use stepper motors, in this example. The stepper motors and servo motors can all be programmed very precisely to 0.002 inch for positioning the glass mandrels 178 relative to the shoes 308, 310, relative to the insert table 312, and relative to the air nipple table 306.

The present invention has been used in experimental or test runs to produce polyurethane condoms 307 having thicknesses ranging from 0.035 mm to 0.060 mm, and lengths from 175 mm to 190 mm. The condoms 307 had a tapered configuration.

Figure 28A:
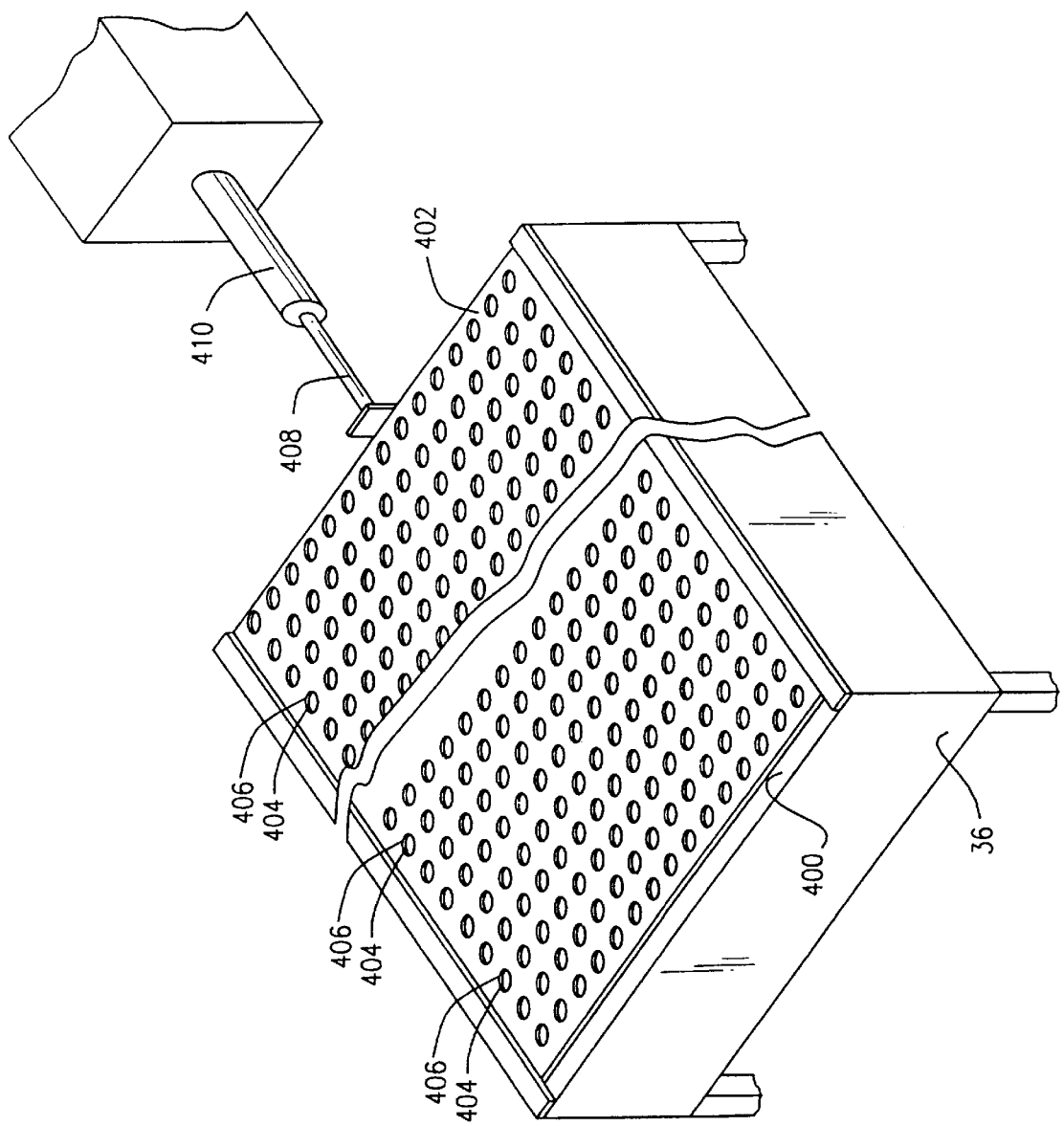
FIG. 28A shows a simplified partial pictorial view of a dipping solution tank having a sliding cover in an open position for permitting glass mandrels to be dipped into the tank.
Figure 28B:
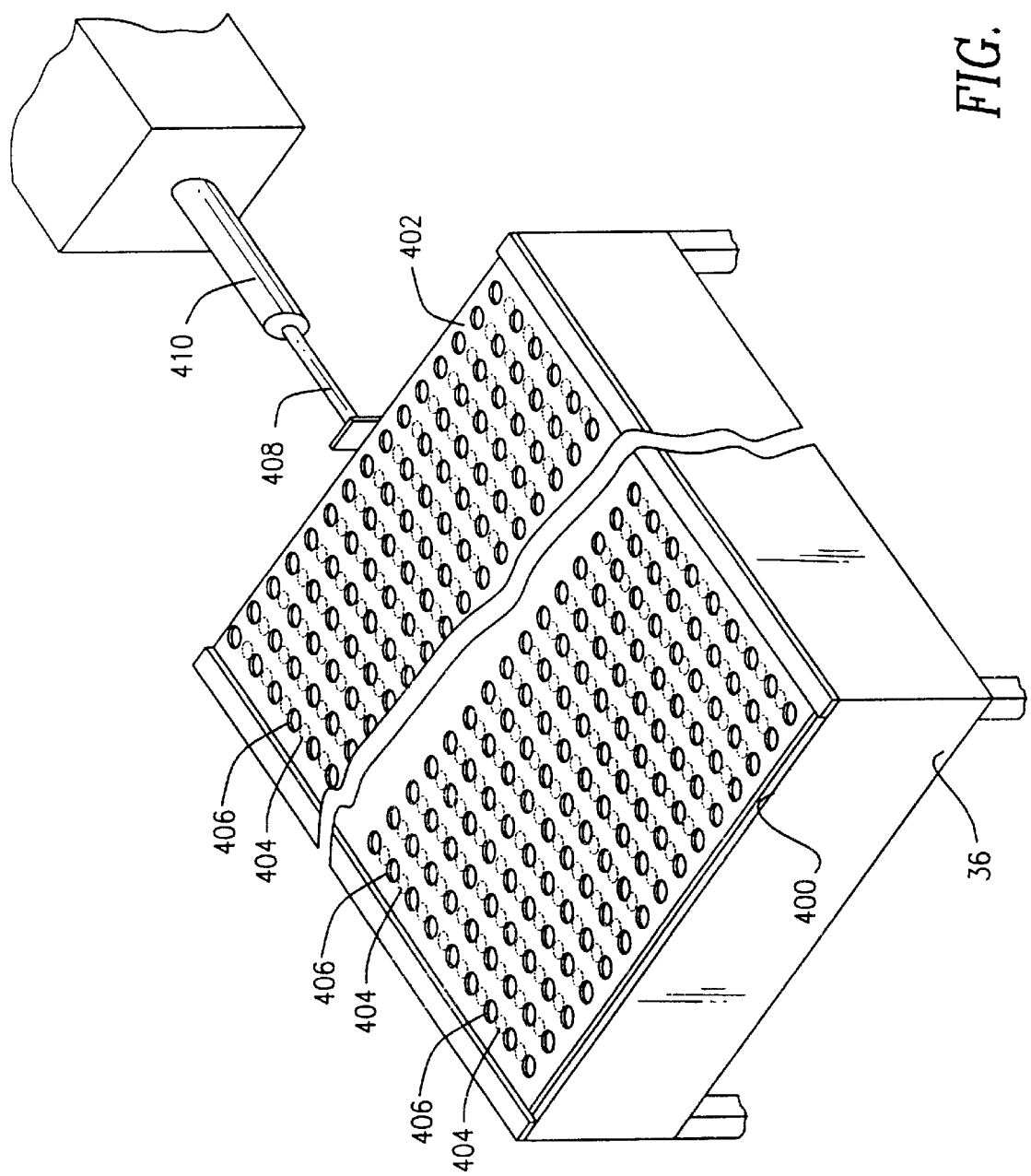
FIG. 28B shows the pictorial view of FIG. 28A with the sliding cover moved to a position to close off holes in the top of the tank to avoid unnecessary evaporation of the dipping solution when not in use.

In another embodiment of the invention, as shown in FIG. 28A, the previously mentioned reservoir dipping tank 36 of polyurethane material dissolved in THF (see FIG. 1B) includes a sliding top cover plate 402 that includes holes 406, as shown. The top 400 of tank 36 includes holes 404. A drive arm 408 of an air cylinder 410 is attached to one end of the sliding plate 402 for selectively moving the sliding plate 402 between a first or open position (see FIG. 28A) for exposing holes 404 through associated holes 406, and a closed position (see FIG. 28B) for substantially closing off the holes 404 in the top 400 of the tank 36. In the open or dipping position of the sliding plate 402, the holes 406 are in a position where they are concentric with associated underlying holes 404 through the otherwise closed off top 400 of the dipping tank 36. In this open position, the holes 406 of the sliding plate 402, and the underlying associated holes 404 in the top 400 of the tank 36 are respectively each configured to have the minimum diameter required for permitting an associated mandrel 178 to be passed through the holes into the dipping solution in the tank 36. By maintaining the minimum diameter necessary for the plurality of overlying holes 406 and 404, respectively, the THP concentration about the associated mandrels 178 is kept substantially rich or high as the mandrels 178 are withdrawn from the tank 36 to prevent premature rapid evaporation of the THF solvent, for in turn permitting control of the withdrawal rate. Also, by maintaining a high concentration of THF vapors about the mandrels 178 as they are dipped into the dipping solution contained in tank 36, the entry rate of dipping can be more finely controlled to minimize film defects.

Although various embodiments of the invention are shown and described herein, they are not meant to be limiting. Various modifications may occur to those of skill in the art, which modifications are meant to be covered by the spirit and scope of the appended claims. For example, with certain modification, the present system of the invention can be used to produce other than condom products, such as catheters and other medical devices, finger cots, gloves, coating processors, and so forth. Also, in an alternative embodiment, the takeoff inserts 312 can be eliminated by making the underlying holes in insert table 304 (see FIG. 9) to each have a chamfer and a diameter less than that of a rolled up condom 307. However, the preferred embodiment of the invention includes the takeoff inserts 312.

What is claimed is:

1. A method for making a thin film prophylactic device comprising the steps of:
   providing a reservoir including polyurethane material dissolved in a tetrahydrofuran (THF) solvent as a dipping solution;
   dipping vertically a mandrel having the general shape of the device into said dipping solution, said mandrel having an axis of symmetry about its longitudinal axis;
   rotating the mandrel radially at least about its longitudinal axis while dipping, after it has been withdrawn from the reservoir, and before all the solvent has been evaporated from the film;
   withdrawing vertically the mandrel from the reservoir so as to deposit a film on the mandrel; and
   evaporating the solvent from the film.

2. A method as set forth in claim 1, wherein said of rotating includes rotating said mandrel radially about its longitudinal axis selectively in clockwise and/or counterclockwise directions.

3. A method as set forth in claim 2, wherein the rotating simultaneously includes rotation about a different axis at predetermined times.

4. A method as set forth in claim 1 further comprising the step of:
cooling the mandrel before it is dipped into the reservoir.

5. A method as set forth in claim 4, wherein the step of cooling is performed for providing gradual cooling.

6. A method as set forth in claim 5, wherein the step of cooling via gradual cooling is performed in a plurality of discrete steps.

7. A method as set forth in claim 1, further comprising the step of:
providing an inert atmosphere to lower or remove the $O_2$ therein to prevent combustion of solvent, and to maintain a moisture free atmosphere, in which the steps of claim 1 are performed.

8. A method as set forth in claim 7, further including the steps of:
controlling the concentration of solvent in the inert atmosphere to control the evaporation rate in said evaporating step.

9. A method as set forth in claim 7, further including the step of controlling the flow rate of said inert atmosphere past said mandrel, to control the evaporation rate in said evaporating step.

10. A method as set forth in claim 7, further including the step of controlling the temperature of the inert atmosphere to control the evaporation rate in said evaporating step.

11. A method as set forth in claim 1, further comprising the step of:
reducing the concentration of oxygen in the atmosphere to a safe level where the steps of dipping and evaporating are performed.

12. A method as set forth in claim 11, wherein the reduction of the concentration of oxygen is attained by introducing an inert gas.

13. A method as set forth in claim 1, further comprising the step of maintaining the viscosity of said dipping solution in the reservoir within a given range.

14. A method as set forth in claim 1, further comprising providing a pressure greater than atmospheric pressure for said dipping, withdrawing, and evaporating steps.

15. A method as set forth in claim 1, further including the step of controlling the temperature of said dipping solution, to partially control both the thickness of said film and the evaporation rate in said evaporating step.

16. A method as set forth in claim 1, further including the step of controlling the viscosity of said dipping solution to control the thickness of said film deposited on said mandrel.

17. A method as set forth in claim 1, further including the step of providing an enriched atmosphere of said solvent proximate the surface of said dipping solution during said withdrawing step, to substantially reduce the rate of solvent evaporation from the film at that time.

18. A method as set forth in claim 1, further including in said withdrawing step the step of controlling the rate of withdrawal of said mandrel from said reservoir to control the thickness of said film on said mandrel.

19. A method as set forth in claim 1, further including in said dipping step the step of controlling the rate of dipping said mandrel into said dipping solution to minimize film defects.

20. A method as set forth in claim 1, further including the steps of:
removing the film formed into a prophylactic device from said mandrel; and
tumbling said prophylactic device in a tumbler until the polyurethane material substantially completes its crystallization to prevent wrinkling of said prophylactic device.

21. A method for making a thin film prophylactic device comprising the steps of:
providing a reservoir containing a dipping solution of solvent based polyurethane material;
maintaining the temperature of said dipping solution in a range from 50° F. to 70° F.
cooling a mandrel to about the temperature of said dipping solution, said mandrel having the shape of the device to be formed;
dipping the mandrel vertically into the dipping solution;
withdrawing the mandrel vertically from the reservoir so as to form a film thereon;
evaporating solvent from the film; and
rotating said mandrel radially about its longitudinal axis during at least said dipping, and withdrawing steps.

22. A method as set forth in claim 21, wherein said solvent is tetrahydrofuran.

23. A method as set forth in claim 21, wherein the mandrel is shaped like a condom, and its longitudinal axis is an axis of symmetry, said method further including in the step of rotating said mandrel, rotating it about its axis of symmetry selectively in clockwise and/or counterclockwise directions.

24. A method as set forth in claim 21, wherein the step of rotating said mandrel also simultaneously includes rotation about an axis other than its longitudinal axis.

25. A method as set forth in claim 21, further comprising the steps of passing a mandrel through the steps of claim 22 multiple times so as to form additional film thereon.

26. A method as set forth in claim 21, further including the step of rotating said mandrel during said evaporating step.

27. A method for fabricating a thin film prophylactic device comprising the steps of:
cleaning a mandrel for the device via a cleaning solution;
heating the mandrel to dry it;
cooling the temperature of the mandrel to be proximate the temperature of a dipping solution;
dipping the mandrel vertically in and out of said dipping solution consisting of material dissolved in a volatile and flammable solvent so as to form a film on the mandrel;
rotating the mandrel radially about its longitudinal axis while in and after it is withdrawn from the dipping solution;
evaporating the solvent from the film; and
removing the film from the mandrel.

28. A method as set forth in claim 27, wherein:
the steps of cleaning, drying the mandrel and removing the film from it are performed in an air atmosphere; and
the steps of cooling the temperature of the mandrel, dipping it in and out of the reservoir and evaporating solvent from the film are performed in an atmosphere containing safe concentrations of oxygen and solvent by introduction of an inert gas so as to expel sufficient oxygen and solvent vapor to prevent ignition of the solvent.

29. A method as set forth in claim 28, further comprising the step of recovering solvent from that which is expelled.

30. A method as set forth in claim 28, further comprising the steps of:
connecting the mandrel to a source of reference voltage; and
applying powder having an opposite electrical charge to the electrical charge on said mandrel to the film.

31. A method as set forth in claim 30, wherein the mandrel consists of electrically nonconductive material, and is made electrically conductive by coating it with electrically conductive material and applying said source of reference voltage to the conductive material.

32. A method for making a thin film prophylactic device comprising the steps of:
   providing a reservoir including a solvent/carrier and polymeric material as a dipping solution;
   vertically dipping a mandrel having the general shape of the device into said dipping solution;
   vertically withdrawing the mandrel from the reservoir so as to deposit a film on the mandrel;
   evaporating the solvent from the film to dry the film; and
   rotating the mandrel radially about its longitudinal axis while dipping, after it has been withdrawn from the reservoir, and before all the solvent has been evaporated from the film.

33. A method as set forth in claim 32, wherein the mandrel has an axis of symmetry about its longitudinal axis, and the rotating is about said axis selectively in clockwise and/or counterclockwise directions.

34. A method as set forth in claim 33, wherein the rotating is also about a different axis.

35. A method as set forth in claim 32 further comprising the step of:
   cooling the mandrel before it is dipped into the reservoir.

36. A method as set forth in claim 35, wherein the step of cooling is performed for providing gradual cooling.

37. A method as set forth in claim 36, wherein the step of cooling via gradual cooling is performed in a plurality of discrete steps.

38. A method as set forth in claim 32, further comprising the step of:
   preventing an explosive mixture of solvent fumes and oxygen by providing an inert atmosphere in which the steps of claim 32 are performed for volatile solvents.

39. A method as set forth in claim 38, further including the steps of:
   controlling the concentration of solvent in the inert atmosphere to control the evaporation rate in said evaporating step.

40. A method as set forth in claim 38, further including the step of controlling the flow rate of said inert atmosphere past said mandrel, to control the evaporation rate in said evaporating step.

41. A method as set forth in claim 38, further including the step of controlling the temperature of the inert atmosphere to control the evaporation rate in said evaporating step.

42. A method as set forth in claim 32, further comprising the step of:
   reducing the concentration of oxygen in the atmosphere to a safe level to prevent ignition of solvent where the steps of dipping and evaporating are performed for volatile solvents.

43. A method as set forth in claim 42, wherein the reduction of the concentration of oxygen is attained by introducing an inert gas.

44. A method as set forth in claim 32, further comprising the step of maintaining the viscosity of said dipping solution in the reservoir within a given range.

45. A method as set forth in claim 32, further comprising providing a pressure greater than atmospheric pressure for said dipping, withdrawing, and evaporating steps.

46. A method as set forth in claim 32, further including the step of controlling the temperature of said dipping solution, to partially control both the thickness of said film and the evaporation rate in said evaporating step.

47. A method as set forth in claim 32, further including the step of controlling the viscosity of said dipping solution to control the thickness of said film deposited on said mandrel.

48. A method as set forth in claim 32, further including the step of providing an enriched atmosphere of said solvent/carrier proximate the surface of said dipping solution during said withdrawing step, to substantially reduce the rate of solvent/carrier evaporation from the film at that time.

49. A method as set forth in claim 32, further including in said withdrawing step the step of controlling the rate of withdrawal of said mandrel from said reservoir to control the thickness of said film on said mandrel.

50. A method as set forth in claim 32, further including in said dipping step the step of controlling the rate of dipping said mandrel into said dipping solution to minimize film defects.

51. A method as set forth in claim 32, further including the steps of:
   removing the film formed into a prophylactic device from said mandrel; and
   tumbling said prophylactic device in a tumbler until the polymeric material substantially completes its crystallization to prevent wrinkling of said prophylactic device.

52. A method for making a thin film prophylactic device comprising the steps of:
   forming a mandrel consisting of glass to have the shape of the device that is to be formed;
   providing a reservoir of a dipping solution consisting of a solvent/carrier based polymeric material;
   maintaining the dipping solution at a desired temperature;
   maintaining the mandrel at a temperature close to said desired temperature for preventing cracking of said mandrel when dipped into said dipping solution;
   dipping the mandrel vertically into the solvent carrier based polymeric material;
   withdrawing the mandrel vertically from the reservoir so as to form a film thereon;
   evaporating solvent from the film; and
   rotating said mandrel radially about its longitudinal axis during said dipping, withdrawing, and evaporating steps.

53. A method as set forth in claim 51, wherein the mandrel is shaped like a condom and its longitudinal axis is an axis of symmetry, said method further including in the step of rotating said mandrel, rotating it radially about its axis of symmetry selectively in clockwise and/or counterclockwise directions.

54. A method as set forth in claim 53, wherein the step of rotating also includes simultaneous rotation of said mandrel about an axis other than radially about its axis of symmetry.

55. A method as set forth in claim 52, further comprising the steps of passing a mandrel through the steps of claim 52 multiple times so as to form additional film thereon.

56. A method for fabricating a thin film prophylactic device comprising the steps of:
   cleaning a mandrel for the device via a cleaning solution;
   heating the mandrel to dry it;
   cooling the mandrel to a desired temperature;
   vertically dipping the mandrel in and out of a reservoir of polymeric material dissolved in a solvent/carrier maintained at said desired temperature so as to form a film on the mandrel;

rotating the mandrel radially about its longitudinal axis while in, during withdrawal, and after it is withdrawn from the reservoir;

evaporating the solvent/carrier from the film to dry the film; and removing the film from the mandrel.

57. A method as set forth in claim 56, wherein:

the steps of cleaning, drying the mandrel and removing the film from it are performed in an air atmosphere; and the steps of cooling the mandrel, dipping it in and out of the reservoir and evaporating solvent/carrier from the film are performed in an atmosphere containing safe concentrations of oxygen and solvent/carrier by introduction of an inert gas so as to expel oxygen and solvent/carrier to substantially prevent any chance of combustion of said solvent/carrier.

58. A method as set forth in claim 57, further comprising the step of recovering solvent/carrier from that which is expelled.

59. A method as set forth in claim 57, further comprising the steps of:

connecting the mandrel to a source of reference voltage; and applying powder having an opposite electrical charge to the electrical charge on said mandrel to the film.

60. A method as set forth in claim 59, wherein the mandrel consists of electrically nonconductive material, and is made electrically conductive by coating it with electrically conductive material and applying said source of reference voltage to the conductive material.

* * * * *